US 11,704,917 B2

(12) United States Patent
Kuo et al.

(10) Patent No.: US 11,704,917 B2
(45) Date of Patent: Jul. 18, 2023

(54) MULTI-SENSOR ANALYSIS OF FOOD

(71) Applicant: Infineon Technologies AG, Neubiberg (DE)

(72) Inventors: Cynthia Kuo, Mountain View, CA (US); Maher Matta, Sunnyvale, CA (US); Avik Santra, Munich (DE)

(73) Assignee: Infineon Technologies AG, Neubiberg (DE)

( * ) Notice: Subject to any disclaimer, the term of this patent is extended or adjusted under 35 U.S.C. 154(b) by 149 days.

(21) Appl. No.: 17/368,570

(22) Filed: Jul. 6, 2021

(65) Prior Publication Data

US 2022/0012467 A1    Jan. 13, 2022

Related U.S. Application Data

(60) Provisional application No. 63/049,823, filed on Jul. 9, 2020.

(51) Int. Cl.
| | | |
|---|---|---|
| *G01S 13/86* | (2006.01) | |
| *G06V 20/64* | (2022.01) | |
| *G06T 7/00* | (2017.01) | |
| *G06V 10/82* | (2022.01) | |
| *G16H 20/60* | (2018.01) | |
| *G06V 20/68* | (2022.01) | |

(52) U.S. Cl.
CPC .......... *G06V 20/647* (2022.01); *G01S 13/867* (2013.01); *G06T 7/0004* (2013.01); *G06V 10/82* (2022.01); *G06T 2207/30128* (2013.01); *G06V 20/68* (2022.01); *G16H 20/60* (2018.01)

(58) Field of Classification Search
None
See application file for complete search history.

(56) References Cited

U.S. PATENT DOCUMENTS

| | | | |
|---|---|---|---|
| 4,241,347 | A | 12/1980 | Albanese et al. |
| 6,147,572 | A | 11/2000 | Kaminski et al. |
| 6,414,631 | B1 | 7/2002 | Fujimoto |
| 6,636,174 | B2 | 10/2003 | Arikan et al. |
| 7,048,973 | B2 | 5/2006 | Sakamoto et al. |
| 7,057,564 | B2 | 6/2006 | Tsai et al. |
| 7,171,052 | B2 | 1/2007 | Park |
| 7,317,417 | B2 | 1/2008 | Arikan et al. |

(Continued)

FOREIGN PATENT DOCUMENTS

| | | |
|---|---|---|
| CN | 1463161 A | 12/2003 |
| CN | 1716695 A | 1/2006 |

(Continued)

OTHER PUBLICATIONS

"BT24MTR11 Using BGT24MTR11 in Low Power Applications 24 GHz Rader," Application Note AN341, Revision: Rev 1.0, Infineon Technologies AG, Munich, Germany, Dec. 2, 2013, 25 pages.

(Continued)

*Primary Examiner* — Idowu O Osifade
(74) *Attorney, Agent, or Firm* — Slater Matsil, LLP

(57) ABSTRACT

In an embodiment, a method for estimating a composition of food includes: receiving a first three-dimensional (3D) image; identifying food in the first 3D image; determining a volume of the identified food based on the first 3D image; and estimating a composition of the identified food using a millimeter-wave radar.

31 Claims, 11 Drawing Sheets

(56) References Cited

U.S. PATENT DOCUMENTS

| | | |
|---|---|---|
| 7,596,241 B2 | 9/2009 | Rittscher et al. |
| 7,692,574 B2 | 4/2010 | Nakagawa |
| 7,873,326 B2 | 1/2011 | Sadr |
| 7,889,147 B2 | 2/2011 | Tam et al. |
| 8,228,382 B2 | 7/2012 | Pattikonda |
| 8,497,805 B2 | 7/2013 | Rofougaran et al. |
| 8,659,369 B2 | 2/2014 | Rofougaran et al. |
| 8,731,502 B2 | 5/2014 | Salle et al. |
| 8,836,596 B2 | 9/2014 | Richards et al. |
| 8,847,814 B2 | 9/2014 | Himmelstoss et al. |
| 8,860,532 B2 | 10/2014 | Gong et al. |
| 8,976,061 B2 | 3/2015 | Chowdhury |
| 9,172,132 B2 | 10/2015 | Kam et al. |
| 9,182,476 B2 | 11/2015 | Wintermantel |
| 9,202,105 B1 | 12/2015 | Wang et al. |
| 9,413,079 B2 | 8/2016 | Kamgaing et al. |
| 9,495,600 B2 | 11/2016 | Heu et al. |
| 9,886,095 B2 | 2/2018 | Pothier |
| 9,935,065 B1 | 4/2018 | Baheti et al. |
| 10,795,012 B2 | 10/2020 | Santra et al. |
| 2003/0179127 A1 | 9/2003 | Wienand |
| 2004/0238857 A1 | 12/2004 | Beroz et al. |
| 2006/0001572 A1 | 1/2006 | Gaucher et al. |
| 2006/0049995 A1 | 3/2006 | Imaoka et al. |
| 2006/0067456 A1 | 3/2006 | Ku et al. |
| 2007/0210959 A1 | 9/2007 | Herd et al. |
| 2008/0106460 A1 | 5/2008 | Kurtz et al. |
| 2008/0238759 A1 | 10/2008 | Carocar et al. |
| 2008/0291115 A1 | 11/2008 | Doan et al. |
| 2008/0308917 A1 | 12/2008 | Pressel et al. |
| 2009/0073026 A1 | 3/2009 | Nakagawa |
| 2009/0085815 A1 | 4/2009 | Jakab et al. |
| 2009/0153428 A1 | 6/2009 | Rofougaran et al. |
| 2009/0315761 A1 | 12/2009 | Walter et al. |
| 2010/0207805 A1 | 8/2010 | Haworth |
| 2011/0299433 A1 | 12/2011 | Darabi et al. |
| 2012/0087230 A1 | 4/2012 | Guo et al. |
| 2012/0092284 A1 | 4/2012 | Rofougaran et al. |
| 2012/0116231 A1 | 5/2012 | Liao et al. |
| 2012/0179665 A1* | 7/2012 | Baarman ............... G16H 20/60 707/E17.014 |
| 2012/0195161 A1 | 8/2012 | Little et al. |
| 2012/0206339 A1 | 8/2012 | Dahl |
| 2012/0265486 A1 | 10/2012 | Klofer et al. |
| 2012/0268314 A1 | 10/2012 | Kuwahara et al. |
| 2012/0280900 A1 | 11/2012 | Wang et al. |
| 2013/0027240 A1 | 1/2013 | Chowdhury |
| 2013/0106673 A1 | 5/2013 | McCormack et al. |
| 2014/0028542 A1 | 1/2014 | Lovitt et al. |
| 2014/0070994 A1 | 3/2014 | Schmalenberg et al. |
| 2014/0145883 A1 | 5/2014 | Baks et al. |
| 2014/0324888 A1 | 10/2014 | Xie et al. |
| 2015/0181840 A1 | 7/2015 | Tupin, Jr. et al. |
| 2015/0185316 A1 | 7/2015 | Rao et al. |
| 2015/0212198 A1 | 7/2015 | Nishio et al. |
| 2015/0243575 A1 | 8/2015 | Strothmann et al. |
| 2015/0277569 A1 | 10/2015 | Sprenger et al. |
| 2015/0325925 A1 | 11/2015 | Kamgaing et al. |
| 2015/0346820 A1 | 12/2015 | Poupyrev et al. |
| 2015/0348821 A1 | 12/2015 | Iwanaga et al. |
| 2015/0364816 A1 | 12/2015 | Murugan et al. |
| 2016/0018511 A1 | 1/2016 | Nayyar et al. |
| 2016/0041617 A1 | 2/2016 | Poupyrev |
| 2016/0041618 A1 | 2/2016 | Poupyrev |
| 2016/0061942 A1 | 3/2016 | Rao et al. |
| 2016/0061947 A1 | 3/2016 | Patole et al. |
| 2016/0098089 A1 | 4/2016 | Poupyrev |
| 2016/0103213 A1 | 4/2016 | Ikram et al. |
| 2016/0109566 A1 | 4/2016 | Liu et al. |
| 2016/0118353 A1 | 4/2016 | Ahrens et al. |
| 2016/0135655 A1 | 5/2016 | Ahn et al. |
| 2016/0146931 A1 | 5/2016 | Rao et al. |
| 2016/0146933 A1 | 5/2016 | Rao et al. |
| 2016/0178730 A1 | 6/2016 | Trotta et al. |
| 2016/0187462 A1 | 6/2016 | Altus et al. |
| 2016/0191232 A1 | 6/2016 | Subburaj et al. |
| 2016/0223651 A1 | 8/2016 | Kamo et al. |
| 2016/0240907 A1 | 8/2016 | Haroun |
| 2016/0249133 A1 | 8/2016 | Sorensen |
| 2016/0252607 A1 | 9/2016 | Saboo et al. |
| 2016/0259037 A1 | 9/2016 | Molchanov et al. |
| 2016/0266233 A1 | 9/2016 | Mansour |
| 2016/0269815 A1 | 9/2016 | Liao et al. |
| 2016/0291130 A1 | 10/2016 | Ginsburg et al. |
| 2016/0299215 A1 | 10/2016 | Dandu et al. |
| 2016/0306034 A1 | 10/2016 | Trotta et al. |
| 2016/0320852 A1 | 11/2016 | Poupyrev |
| 2016/0320853 A1 | 11/2016 | Lien et al. |
| 2016/0327633 A1 | 11/2016 | Kumar Y.B. et al. |
| 2016/0334502 A1 | 11/2016 | Ali et al. |
| 2016/0349845 A1 | 12/2016 | Poupyrev et al. |
| 2017/0033062 A1 | 2/2017 | Liu et al. |
| 2017/0045607 A1 | 2/2017 | Bharadwaj et al. |
| 2017/0052618 A1 | 2/2017 | Lee et al. |
| 2017/0054449 A1 | 2/2017 | Mani et al. |
| 2017/0060254 A1 | 3/2017 | Molchanov et al. |
| 2017/0070952 A1 | 3/2017 | Balakrishnan et al. |
| 2017/0074974 A1 | 3/2017 | Rao et al. |
| 2017/0074980 A1 | 3/2017 | Adib et al. |
| 2017/0090014 A1 | 3/2017 | Subburaj et al. |
| 2017/0090015 A1 | 3/2017 | Breen et al. |
| 2017/0115377 A1 | 4/2017 | Giannini et al. |
| 2017/0131395 A1 | 5/2017 | Reynolds et al. |
| 2017/0139036 A1 | 5/2017 | Nayyar et al. |
| 2017/0141453 A1 | 5/2017 | Waelde et al. |
| 2017/0170947 A1 | 6/2017 | Yang |
| 2017/0176574 A1 | 6/2017 | Eswaran et al. |
| 2017/0192847 A1 | 7/2017 | Rao et al. |
| 2017/0201019 A1 | 7/2017 | Trotta |
| 2017/0212597 A1 | 7/2017 | Mishra |
| 2017/0364160 A1 | 12/2017 | Malysa et al. |
| 2018/0025368 A1* | 1/2018 | Frank ................... G06Q 10/101 705/7.29 |
| 2018/0046255 A1 | 2/2018 | Rothera et al. |
| 2018/0071473 A1 | 3/2018 | Trotta et al. |
| 2018/0101239 A1 | 4/2018 | Yin et al. |
| 2019/0290172 A1* | 9/2019 | Hadad ................... G06N 20/00 |
| 2019/0317191 A1 | 10/2019 | Santra et al. |
| 2020/0225778 A1* | 7/2020 | Lewty ................ G06F 3/04883 |
| 2021/0123872 A1* | 4/2021 | Shaker .............. G06V 40/1306 |
| 2021/0124947 A1* | 4/2021 | Datar ................... G06V 20/52 |

FOREIGN PATENT DOCUMENTS

| | | |
|---|---|---|
| CN | 101490578 A | 7/2009 |
| CN | 101585361 A | 11/2009 |
| CN | 102788969 A | 11/2012 |
| CN | 102967854 A | 3/2013 |
| CN | 103529444 A | 1/2014 |
| CN | 203950036 U | 11/2014 |
| DE | 102008054570 A1 | 6/2010 |
| DE | 102011100907 A1 | 1/2012 |
| DE | 102011075725 A1 | 11/2012 |
| DE | 102014118063 A1 | 7/2015 |
| GB | 2247799 A | 3/1992 |
| JP | 2001174539 A | 6/2001 |
| JP | 2004198312 A | 7/2004 |
| JP | 2006234513 A | 9/2006 |
| JP | 2008029025 A | 2/2008 |
| JP | 2008089614 A | 4/2008 |
| JP | 2009069124 A | 4/2009 |
| JP | 2011529181 A | 12/2011 |
| JP | 2012112861 A | 6/2012 |
| JP | 2013521508 A | 6/2013 |
| JP | 2014055957 A | 3/2014 |
| KR | 20090063166 A | 6/2009 |
| KR | 20140082815 A | 7/2014 |
| WO | 2007060069 A1 | 5/2007 |
| WO | 2013009473 A2 | 1/2013 |
| WO | 2016033361 A1 | 3/2016 |

(56) References Cited

OTHER PUBLICATIONS

Chen, Xiaolong et al., "Detection and Extraction of Marine Target with Micromotion via Short-Time Fractional Fourier Transform in Sparse Domain," IEEE International Conference on Signal Processing, Communications and Computing, CSPCC, Aug. 5-8, 2016, 5 pages.

Chen, Xiaolong et al., "Detection and Extraction of Target with Micromotion in Spiky Sea Clutter via Short-Time Fractional Fourier Transform", IEEE Transactions on Geoscience and Remote Sensing, vol. 52, No. 2, Feb. 2014, pp. 1002-1018.

Chioukh, Lydia et al., "Noise and Sensitivity of Harmonic Radar Architecture for Remote Sensing and Detection of Vital Signs", IEEE Transactions on Microwave Theory and Techniques, vol. 62, No. 9, Sep. 2014, pp. 1847-1855.

Chuanhua, Du, "FMCW Radar Range-Doppler Processing and Beam Formation Technology," Chinese Doctoral Dissertations & Master's Theses Full Text Database (Masters)—Information Science and Technology Series, China National Knowledge Infrastructure, ISSN 1674-0246, CN 11-9144/G, Dec. 16, 2004—Mar. 2015, 14 pages.

Deacon, Peter et al., "Frequency Modulated Continuous Wave (FMCW) Radar," Design Team 6 Technical Lecture, Nov. 9, 2011, 27 pages.

Dham, Vivek "Programming Chirp Parameters in TI Radar Devices," Application Report SWRA553, Texas Instruments, May 2017, 15 pages.

Diederichs, Kailtyn et al., "Wireless Biometric Individual Identification Utilizing Millimeter Waves", IEEE Sensors Letters, vol. 1, No. 1, IEEE Sensors Council 3500104, Feb. 2017, 4 pages.

Dooring Alert Systems, "Riders Matter," http:\\dooringalertsystems.com, printed Oct. 4, 2017, 16 pages.

Filippelli, Mario et al., "Respiratory dynamics during laughter," J Appl Physiol, (90), p. 1441 1446, Apr. 2001, http://ap.physiology.org/content/jap/90/4/1441.full.pdf.

Fox, Ben, "The Simple Technique That Could Save Cyclists' Lives," https://www.outsideonline.com/2115116/simple-technique-could-save-cyclists-lives, Sep. 19, 2016, 6 pages.

Gigie, Andrew et al., "Novel Approach for Vibration Detection Using Indented Radar", Progess in Electromagnetic Research C, vol. 87, pp. 147-162, Oct. 4, 2018.

Gouveia, Carolina et al., "A Review on Methods for Random Motion Detection and Compensation in Bio-Radar Systems", Sensors, MDPI, Jan. 31, 2019, 17 pages.

Gu, Changzhan et al., "Assessment of Human Respiration Patterns via Noncontact Sensing Using Doppler Multi-Radar System", Sensors Mar. 2015, 15(3), 6383-6398, doi: 10.3390/s150306383, 17 pages.

Gu, Changzhan et al., "Deep Neural Network based Body Movement Cancellation for Doppler Radar Vital Sign Detection", IEEE MTT-S International Wireless Symposium (IWS) May 19-22, 2019, 3 pages.

Gu, Changzhu "Short-Range Noncontact Sensors for Healthcare and Other Emerginng Applications: A Review", Sensors, MDPI, Jul. 26, 2016, 24 pages.

Gu, Changzhan et al., "From Tumor Targeting to Speed Monitoring", IEEE Microwave Magazine, ResearchGate, Jun. 2014, 11 pages.

Guercan, Yalin "Super-resolution Algorithms for Joint Range-Azimuth-Doppler Estimation in Automotive Radars," Technische Universitet Delft, TUDelft University of Technology Challenge the Future, Jan. 25, 2017, 72 pages.

Hu, Wei et al., "Noncontact Accurate Measurement of Cardiopulmonary Activity Using a Compact Quadrature Doppler Radar Sensor", IEEE Transactions on Biomedical Engineering, vol. 61, No. 3, Mar. 2014, pp. 725-735.

Immoreev, I. Ya. "Ultrawideband Radars: Features and Capabilities", Journal of Communications Technology and Electronics, ISSN: 1064-2269, vol. 54, No. 1, Feb. 8, 2009, pp. 1-26.

Inac, Ozgur et al., "A Phased Array RFIC with Built-In Self-Test Capabilities," IEEE Transactions on Microwave Theory and Techniques, vol. 60, No. 1, Jan. 2012, 10 pages.

Killedar, Abdulraheem "XWRIxxx Power Management Optimizations—Low Cost LC Filter Solution," Application Report SWRA577, Texas Instruments, Oct. 2017, 19 pages.

Kishore, N. et al., "Millimeter Wave Antenna for Intelligent Transportation Systems Application", Journal of Microwaves, Optoelectronics and Electromagnetic Applications, vol. 17, No. 1, Mar. 2018, pp. 171-178.

Kizhakkel, V., "Pulsed Radar Target Recognition Based on Micro-Doppler Signatures Using Wavelet Analysis", A Thesis, Graduate Program in Electrical and Computer Engineering, Ohio State University, Jan. 2013-May 2013, 118 pages.

Kuehnke, Lutz, "Phased Array Calibration Procedures Based on Measured Element Patterns," 2001 Eleventh International Conference on Antennas and Propagation, IEEE Conf., Publ. No. 480, Apr. 17-20, 2001, 4 pages.

Li, Changzhi et al., "A Review on Recent Advances in Doppler Radar Sensors for Noncontact Healthcare Monitoring", IEEE Transactions on Microwave Theory and Techniques, vol. 61, No. 5, May 2013, pp. 2046-2060.

Li, Changzhi et al., "A Review on Recent Progress of Portable Short-Range Noncontact Microwave Radar Systems", IEEE Transactions on Microwave Theory and Techniques, vol. 65, No. 5, May 2017, pp. 1692-1706.

Li, Changzhi et al., "Random Body Movement Cancellation in Doppler Radar Vital Sign Detection", IEEE Transactions on Microwave Theory and Techniques, vol. 56, No. 12, Dec. 2008, pp. 3143-3152.

Li, Changzhi et al., "Robust Overnight Monitoring of Human Vital Signs by a Non-contact Respiration and Heartbeat Detector", IEEE Proceedings of the 28th EMBS Annual International Conference, FrA05.5, Aug. 30-Sep. 3, 2006, 4 pages.

Li, Changzhi "Vital-sign monitoring on the go", Sensors news and views, www.nature.com/naturelectronics, Nature Electronics, vol. 2, Jun. 2019, 2 pages.

Liang, Y. et al., "Deep Learning-Based Food Calorie Estimation Method In Dietary Assessment," Journal of Food Engineering, Feb. 18, 2018, 13 pages.

Lim, Soo-Chui et al., "Expansion of Smartwatch Touch Interface from Touchscreen to Around Device Interface Using Infrared Line Image Sensors," Sensors 2015, ISSN 1424-8220, vol. 15, 16642-16653, doi:10.3390/s150716642, www.mdpi.com/journal/sensors, Jul. 15, 2009, 12 pages.

Lin, Jau-Jr et al., "Design of an FMCW radar baseband signal processing system for automotive application," SpringerPlus a SpringerOpen Journal, (2016) 5:42, http://creativecommons.org/licenses/by/4.0/, DOI 10.1186/s40064-015-1583-5; Jan. 2016, 16 pages.

Massagram, Wansuree et al., "Assessment of Heart Rate Variability and Respiratory Sinus Arrhythmia via Doppler Radar", IEEE Transactions on Microwave Theory and Techniques, vol. 57, No. 10, Oct. 2009, pp. 2542-2549.

Meng, Z. et al., "Microwave Sensor Technologies for Food Evaluation and Analysis—Methods, Challenges and Solutions," The University of Manchester Research, Transactions of the Institute of Measurement and Control, Sep. 20, 2017, 18 pages.

Mercuri, Marco et al., "Vital-sign monitoring and spatial tracking of multiple people using a contactless radar-based sensor", Nature Electronics, vol. 2, Articles, https://doi.org/10.1038/s41928-019-0258-6, Jun. 2019, 13 pages.

Mezgec, S. et al., "NutriNet: A Deep Learning Food and Drink Image Recognition System for Dietary Assessment," Nutrients, MDPI, Jun. 27, 2017, 25 pages.

Microwave Journal Frequency Matters, "Single-Chip 24 GHz Radar Front End," Infineon Technologies AG, www.microwavejournal.com/articles/print/21553-single-chip-24-ghz-radar-front-end, Feb. 13, 2014, 2 pages.

Mostov, K., et al., "Medical applications of shortwave FM radar: Remote monitoring of cardiac and respiratory motion", Am. Assoc. Phys. Med., 37(3), Mar. 2010, pp. 1332-1338.

(56) References Cited

OTHER PUBLICATIONS

Muzio, F. et al., "Effects of Moderate Variations in the Macronutrient Content of the Diet on Cardiovascular Disease Risk Factors in Obese Patients With the Metabolic Syndrome," The American Journal of Clinical Nutrition, vol. 86, Issue 4, Oct. 2007, 22 pages.

Myers, A. et al., "Im2Calories: Towards an Automated Mobile Vision Food Diary," 2015 IEEE International Conference on Computer Vision (ICCV), Feb. 18, 2016, 9 pages.

Oguntala, G et al., "Indoor location identification technologies for real-time IoT-based applications: an inclusive survey", Elsevier Inc., http://hdl.handle.net/10454/16634, Oct. 2018, 21 pages.

Olafenwa, M., "Train Image Recognition AI With 5 Lines of code," Towards Data Science, https://towardsdatascience.com/train-image-recognition-ai-with-5-lines-of-code-8ed0bdd8d9ba, Jul. 20, 2018, 12 pages.

Passio, "Pilots and Custom Development," https://www.passiolife.com/services-and-products, Jun. 19, 2020, 3 pages.

Passio, "The Future of Food Intelligence," https://www.passiolife.com, Downloaded Jun. 19, 2020, 3 pages.

Passio, "Unlock the Power Ff Nutrition Data," https://www.passiolife.com/products, Downloaded Jun. 19, 2020, 3 pages.

Peng, Zhengyu et al., "A Portable FMCW Interferometry Radar with Programmable Low-IF Architecture for Localization, ISAR Imaging, and Vial Sign Tracking", IEEE Transactions on Microwave Theory and Techniques, Dec. 15, 2016, 11 pages.

Qadir, Shahida G., et al., "Focused ISAR Imaging of Rotating Target in Far-Field Compact Range Anechoic Chamber," 14th International Conference on Aerospace Sciences & Aviation Technology, ASAT-14-241-IP, May 24-26, 2011, 7 pages.

Richards, Mark A., "Fundamentals of Radar Signal Processing," McGraw Hill Electronic Engineering, ISBN: 0-07-144474-2, Jun. 2005, 93 pages.

Sakamoto, Takuya et al., "Feature-Based Correlation and Topological Similarity for Interbeat Interval Estimation Using Ultrawideband Radar", IEEE Transactions on Biomedical Engineering, vol. 63, No. 4, Apr. 2016, pp. 747-757.

Santra, Avik et al., "Short-range multi-mode continuous-wave radar for vital sign measurement and imaging", ResearchGate, Conference Paper, Apr. 2018, 6 pages.

Schroff, Florian et al., "FaceNet: A Unified Embedding for Face Recognition and Clustering," CVF, CVPR2015, IEEE Computer Society Conference on Computer Vision and Pattern Recognition; Mar. 12, 2015, pp. 815-823.

Simon, W., et al., "Highly Integrated KA-Band Tx Frontend Module Including 8x8 Antenna Array," IMST GmbH, Germany, Asia Pacific Microwave Conference, Dec. 7-10, 2009, 63 pages.

Singh, Aditya et al., "Data-Based Quadrature Imbalance Compensation for a CW Doppler Radar System", https://www.researchgate.net/publication/258793573, IEEE Transactions on Microwave Theory and Techniques, Apr. 2013, 7 pages.

Smartplate, "Your Personal Nutritionist. ®," https://getsmartplate.com, Jun. 19, 2020, 7 pages.

Specim Spectral Imaging, "Highest Nut Quality With Optical Inspection," www.specim.fi, Downloaded Jun. 19, 2020, 2 pages.

Specim Spectral Imaging, "Inspecting Heat Sealed Packages," https://www.specim.fi/inspecting-heat-sealed-packages/, Sep. 27, 2018, 9 pages.

Specim Spectral Imaging, "What's Really in Your Meat? Improve Safety and Quality Save Money By Reducing Waste," www.specim.fi, Downloaded Jun. 19, 2020, 2 pages.

St Andrews HCI Research Group, "Radar and Object Recognition," https://sachi.cs.st-andrews.ac.uk/research/interaction/radarcat-exploits-googles-soli-radar-sensor-for-object-and-material-recognition/, Jun. 19, 2020, 5 pages.

Steinbaeck, J. et al., "Design of a Low-Level Radar and Time-of-Flight Sensor Fusion Framework," ResearchGate, https://www.researchgate.net/publication/327776267, Sep. 20, 2018, 9 pages.

Suleymanov, Suleyman, "Design and Implementation of an FMCW Radar Signal Processing Module for Automotive Applications," Master Thesis, University of Twente, Aug. 31, 2016, 64 pages.

Thayaparan, T. et al., "Micro-Doppler Radar Signatures for Intelligent Target Recognition," Defence Research and Development Canada, Technical Memorandum, DRDC Ottawa TM 2004-170, Sep. 2004, 73 pages.

Thayaparan, T. et al., "Intelligent target recognition using micro-Doppler radar signatures," Defence R&D Canada, Radar Sensor Technology III, Proc. of SPIE, vol. 7308, 730817, Dec. 9, 2009, 11 pages.

Tu, Jianxuan et al., "Fast Acquisition of Heart Rate in Noncontact Vital Sign Radar Measurement Using Time-Window-Variation Technique", IEEE Transactions on Instrumentation and Measurement, vol. 65, No. 1, Jan. 2016, pp. 112-122.

Vinci, Gabor et al., "Microwave Interferometer Radar-Based Vital Sign Detection for Driver Monitoring Systems", IEEE MTT-S International Conference on Microwaves for Intelligent Mobility, Apr. 27-29, 2015, 4 pages.

Vinci,, Gabor et al., "Six-Port Radar Sensor for Remote Respiration Rate and Heartbeat Vital-Sign Monitoring", IEEE Transactions on Microwave Theory and Techniques, vol. 61, No. 5, May 2013, pp. 2093-2100.

Wang, Fu-Kang et al., "Wrist Pulse Rate Monitor Using Self-Injection-Locked Radar Technology", Biosensors, MDPI, Oct. 26, 2016, 12 pages.

Weiß, J. et al., "One-Shot Learning for Robust Material Classification Using Millimeter-Wave Radar System," ResearchGate, vol. 1, No. 3, Jul. 2017, 5 pages.

Wikipedia, "3D Reconstruction From Multiple Images," https://en.wikipedia.org/wiki/3D_reconstruction_from_multiple_images, Jul. 9, 2020, 8 pages.

Wilder, Carol N., et al., "Respiratory patterns in infant cry," Canada Journal of Speech, Human Communication Winter, 1974-75, http://cjslpa.ca/files/1974_HumComm_Vol_01/No_03_2-60/Wilder_Baken_HumComm_1974.pdf, pp. 18-34.

Will, Christoph et al., "Advanced Template Matching Algorithm for Instantaneous Heartbeat Detection using Continuous Wave Radar Systems", ResearchGate, May 2017, 5 pages.

Will, Christoph et al., "Human Target Detection, Tracking, and Classification Using 24-GHz FMCW Radar", IEEE Sensors Journal, vol. 19, No. 17, Sep. 1, 2019, pp. 7283-7299.

Will, Christoph et al., "Local Pulse Wave Detection using Continuous Wave Radar Systems", IEEE Journal of Electromagnetics, RF and Microwaves in Medicine and Biology, Oct. 25, 2017, 9 pages.

Will, Christoph et al., "Radar-Based Heart Sound Detection", Scientific Reports, www.nature.com/scientificreports, Jul. 26, 2018, 15 pages.

Xin, Qin et al., "Signal Processing for Digital Beamforming Fmcw SAR," Hindawi Publishing Corporation, Mathematical Problems in Engineering, vol. 2014, Article ID 859890, http://dx.doi.org/10.1155/2014/859890, Apr. 15, 2014, 11 pages.

* cited by examiner

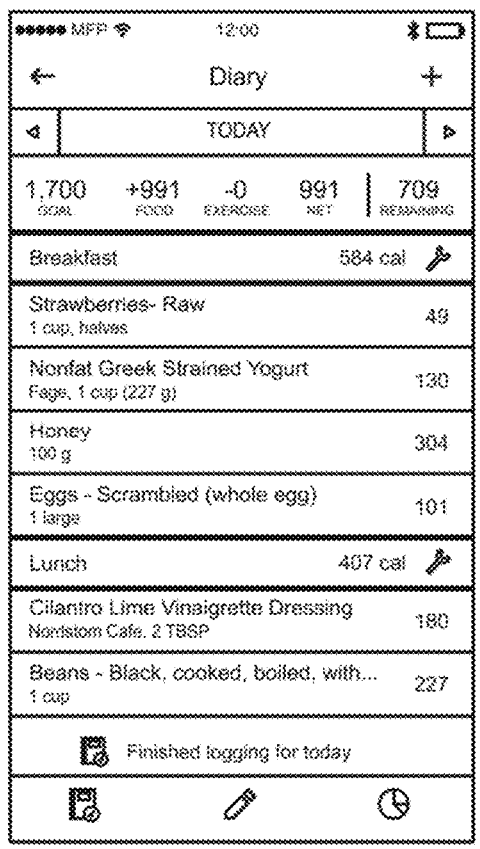
FIG. 1
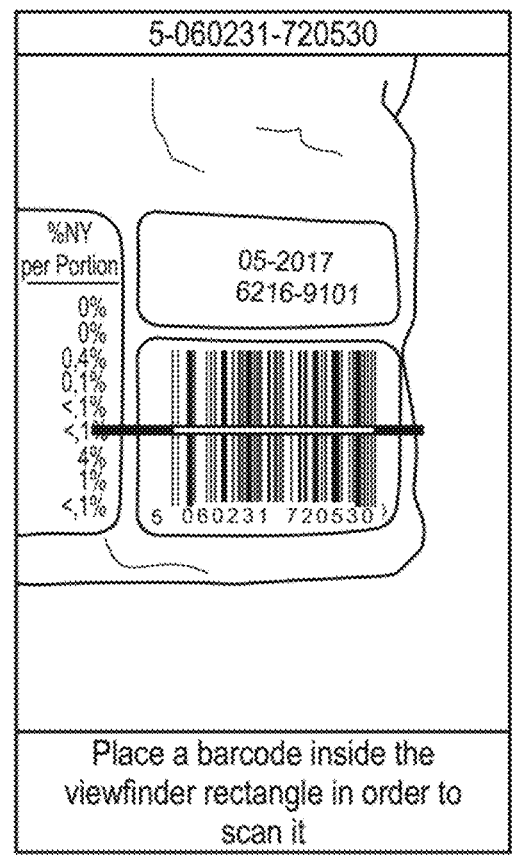
FIG. 2
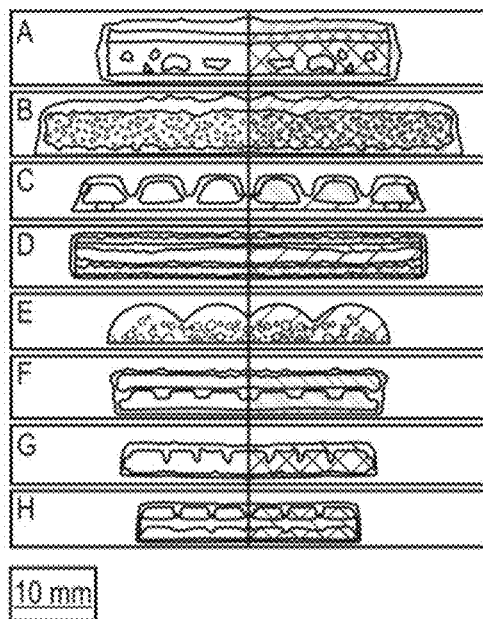
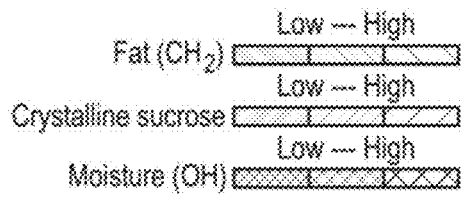
FIG. 3

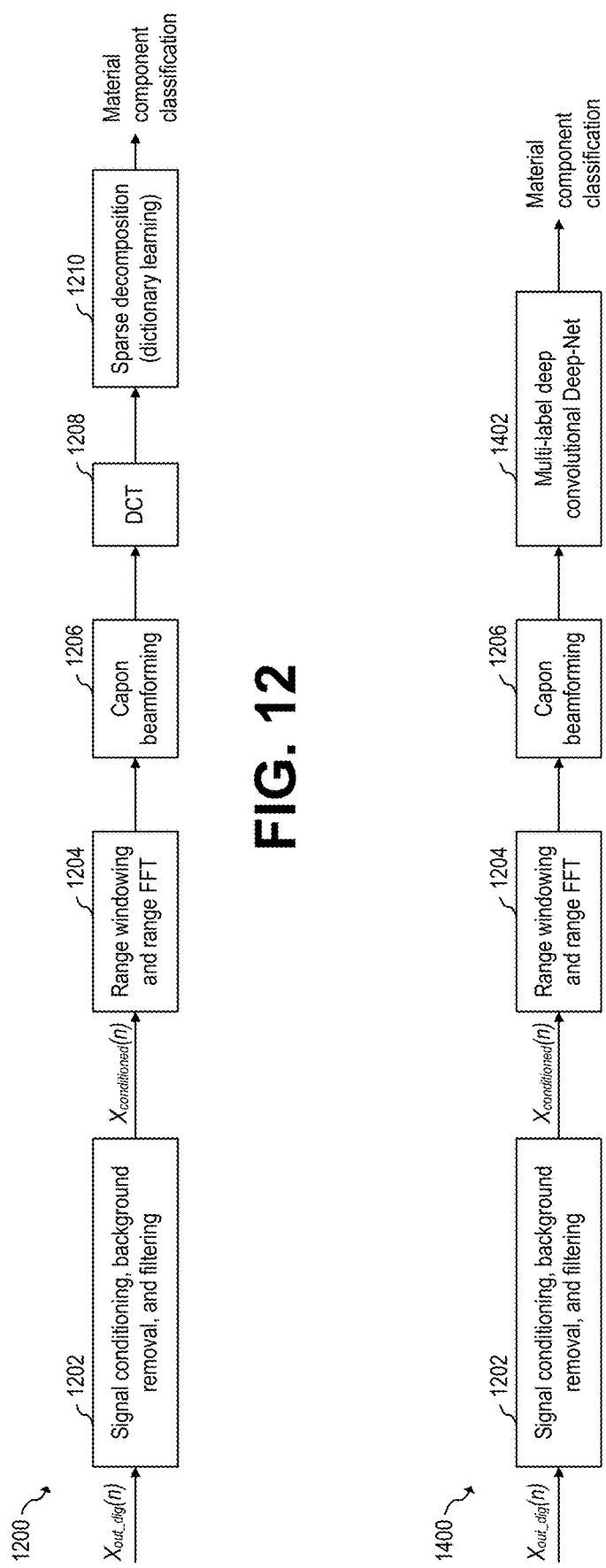

MULTI-SENSOR ANALYSIS OF FOOD

CROSS-REFERENCE TO RELATED APPLICATIONS

This application claims the benefit of U.S. Provisional Application No. 63/049,823, entitled "Multi-Sensor Analysis of Food," and filed on Jul. 9, 2020, which application is hereby incorporated herein by reference.

TECHNICAL FIELD

The present disclosure relates generally to an electronic system and method, and, in particular embodiments, to a multi-sensor analysis of food.

BACKGROUND

Diet and exercise are two of the most important factors in our overall health. For example, poor diet and exercise habits may increase the risk of obesity, heart disease, cancer, diabetes, and other chronic health problems.

Technology companies have tackled the exercise space vigorously, producing a wide range of products, such as connected spinning bikes, step counters, and smartphone apps with guided programs. Diet technology, however, has remained primitive in comparison. Discounting pharmaceutical and surgical solutions for weight loss, diet technology is basically limited to smartphone apps. These apps range from food loggers to platforms that connect dietitians/nutritionists with users to virtual commercial weight loss programs.

Conventional tools and methods for tracking food intake have been mainly limited to manual food logging or camera-based image analysis. For example, FIG. 1 shows an exemplary food logging app.

Manual food logging is generally time-consuming, inconvenient, and cumbersome. For example, in some cases, a user must log every morsel of food that the user consumes consume. In some cases, this requires searching for each ingredient, as well as either estimating or weighing the volume and/or weight of the food consumed. For chain restaurants, the user may be able to find the meal and populate the log automatically. For prepared foods, the user may be able to scan the barcode on the package to access the ingredients and nutritional information. In any case, user input is generally needed, and such input generally requires a substantial amount of work.

SUMMARY

In accordance with an embodiment, a method for estimating a composition of food includes: receiving a first 3D image; identifying food in the first 3D image; determining a volume of the identified food based on the first 3D image; and estimating a composition of the identified food using a millimeter-wave radar.

In accordance with an embodiment, a mobile device includes: a 3D imaging sensor configured to generate a first 3D image; a millimeter-wave radar configured to transmit radar signals and receive reflected radar signals; and a processor configured to: identify food in the first 3D image; determine a volume of the identified food based on the first 3D image; and estimate a composition of the identified food based on the reflected radar signals.

In accordance with an embodiment, A system including: a time-of-flight sensor; a camera; and a millimeter-wave radar configured to transmit radar signals and receive reflected radar signals; and a processor configured to: identify food based on an output of the camera; determine a volume of the identified food based on an output of the time-of-flight sensor; estimate a composition of the identified food based on the reflected radar signals; and determine a quantity of macronutrients of the identified food based on the determined volume and the estimated composition of the identified food.

In accordance with an embodiment, a method for estimating a composition of food includes: receiving radar data from an ADC of a millimeter-wave radar; preprocessing the received radar data to generate a radar image; generating a measurement vector based on the radar image; and estimating a composition of food based on the measurement vector and a first sensing matrix, the first sensing matrix including radar signatures of a plurality of types of food.

BRIEF DESCRIPTION OF THE DRAWINGS

For a more complete understanding of the present invention, and the advantages thereof, reference is now made to the following descriptions taken in conjunction with the accompanying drawings, in which:

FIG. 1 shows an exemplary food logging app;

FIG. 2 shows a conventional way of identifying food using a bar code;

FIG. 3 shows an exemplary composition of various chocolate bars;

FIG. 12 shows a block diagram of an embodiment method for performing food classification using the millimeter-wave radar of FIG. 11, according to an embodiment of the present invention;

FIG. 14 shows a block diagram of an embodiment method for performing food classification using the millimeter-wave radar of FIG. 11, according to an embodiment of the present invention.

Corresponding numerals and symbols in different figures generally refer to corresponding parts unless otherwise

DETAILED DESCRIPTION OF ILLUSTRATIVE EMBODIMENTS

Figure 4:
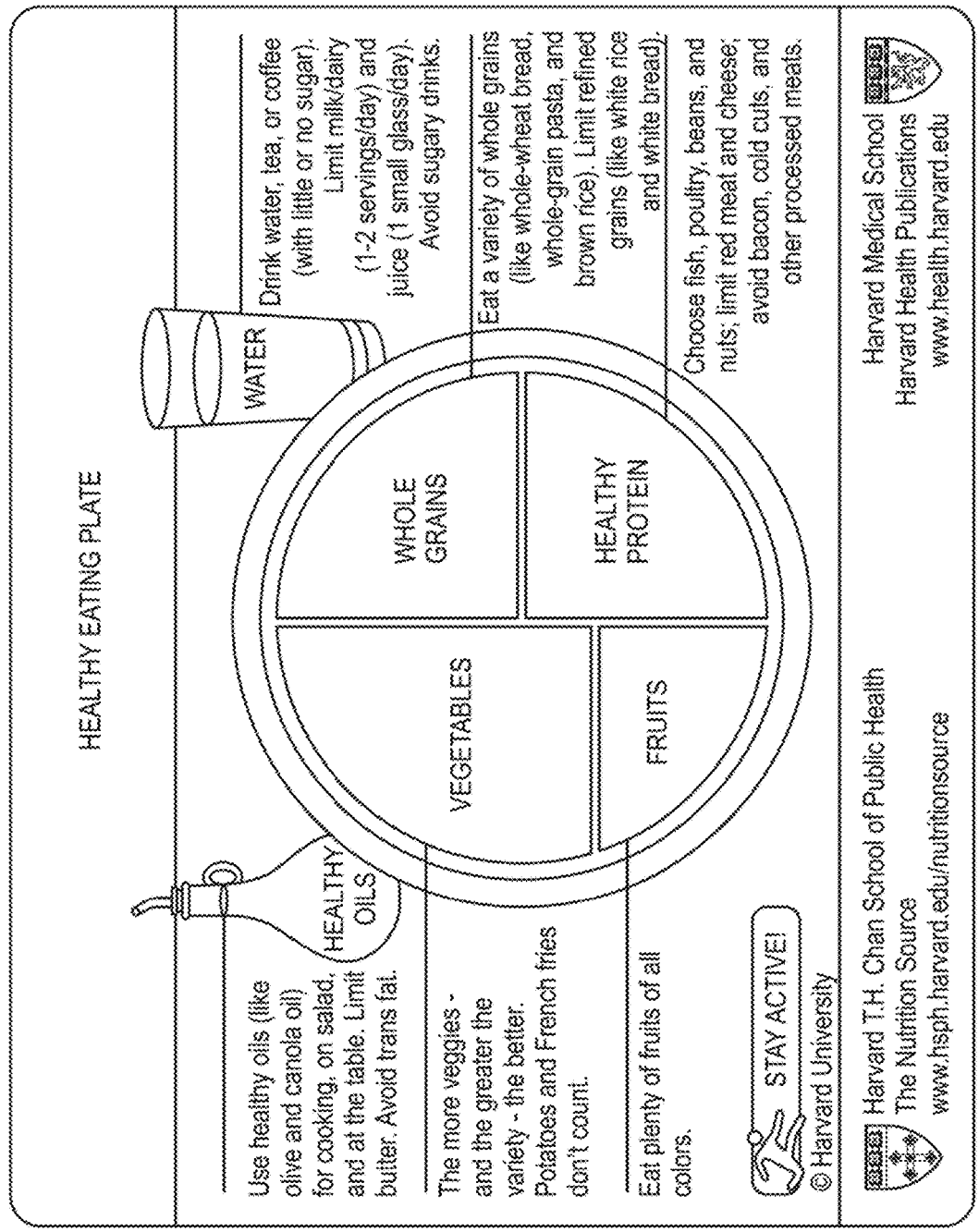
FIG. 4 shows a diagram with an exemplary composition of foods of a healthy diet.

The making and using of the embodiments disclosed are discussed in detail below. It should be appreciated, however, that the present invention provides many applicable inventive concepts that can be embodied in a wide variety of specific contexts. The specific embodiments discussed are merely illustrative of specific ways to make and use the invention, and do not limit the scope of the invention.

The description below illustrates the various specific details to provide an in-depth understanding of several example embodiments according to the description. The embodiments may be obtained without one or more of the specific details, or with other methods, components, materials and the like. In other cases, known structures, materials or operations are not shown or described in detail so as not to obscure the different aspects of the embodiments. References to "an embodiment" in this description indicate that a particular configuration, structure or feature described in relation to the embodiment is included in at least one embodiment. Consequently, phrases such as "in one embodiment" that may appear at different points of the present description do not necessarily refer exactly to the same embodiment. Furthermore, specific formations, structures or features may be combined in any appropriate manner in one or more embodiments.

Embodiments of the present invention will be described in a specific context, a, e.g., 3-dimensional (3D), analysis of food intake, e.g., for mobile devices. Embodiments of the present invention may also be used with devices other than mobile devices. Some embodiments may perform the analysis of food without using 3D techniques. It is understood that the term food includes solid and liquid food, as well as beverages. Some embodiments may be used for analyzing substances other than food.

In an embodiment of the present invention, multiple sensors are fused to support a compelling user experience for tracking food intake. A 3D imaging sensor and a millimeter-wave radar are used to track food consumptions. In some embodiments, a 2D RGB camera is also used to, e.g., improve the accuracy of food classification.

Camera-based loggers may be used to identify the food in a picture, e.g., using image recognition, and to estimate the volume of food. For example, FIG. 2 shows a conventional way of identifying food using a bar code.

With a 2D camera, volume may be estimated by moving the camera and taking images at different angles or by placing the food on a tablecloth or plate of a known size. Other approaches include weighing the food on a smart plate and using a 3D camera to measure the volume of food.

Camera-based loggers, however, may fail to identify food hidden in the image and/or fail to convey relevant details about food preparation, such as the amount of oil used, fat content of meats, sugar or salt content in baked goods, etc. Therefore, it is not unusual for caloric estimates of conventional camera-based loggers to be 20% off. In some cases, in a 2,000 calorie diet, a 20% error could cause a dieter to gain 1 pound every 9 days, where 1 pound is equivalent to 3,500 calories.

In general, calorie-driven food logging may neglect the quality of the food consumed, from a nutritional standpoint.

In industrial applications, such as in the food industry, hyperspectral imaging may be used to analyze food composition for quality control. For example, FIG. 3 shows an exemplary composition of various chocolate bars. Regions high in fat are shown in a first color (e.g., red), while crystalline sucrose and moisture are shown in second and third colors (e.g., green and blue), respectively. Combinations of components may be shown as mixed colors. For example, nuts may be shaded with the first color (e.g., red) indicating high-fat content. Caramel may appear in the third color or a fourth color (e.g., blue or purple) indicating high moisture content with varying fat content. Chocolate may appear in the second color a fifth color (e.g., green, yellow) or a sixth color (e.g., orange) indicating varying combinations of fat and crystalline sucrose.

Hyperspectral imaging is an expensive process—in both computational (image processing) cost and hardware cost—limiting its commercial adoption thus far to industrial applications.

Recent research indicates that it may be advantageous for people to focus on the quality of diet, instead of caloric consumption. Currently, estimating macronutrients (e.g., carbohydrates, proteins, and fats) may be more challenging than counting calories, as it may be tedious to assess the quantity of each food item, look up its macronutrient profile, and tally up the carbohydrates, proteins, and fats. A conventional way to approximate a macronutrient profile with little effort, thus, is to segment the different types of food that is consumed. For example, as shown in FIG. 4, the Harvard School of Public Health recommends ½ of your food should be fruits and vegetables, ¼ should be proteins, and ¼ should be whole grains.

In an embodiment of the present invention, a 3D imaging sensor, such as including a time-of-flight (ToF) sensor, is used to generate a 3D image, which is used to estimate the volume of the food. A millimeter-wave radar is used to estimate the proportion of macronutrients in the food. In some embodiments, the quantity of macronutrients is estimated based on the estimated proportion of macronutrients and the estimated volume of the food. In some embodiments, the proportion of macronutrients in the food is estimated without estimating calories. In some embodiments, focusing on macronutrient composition and avoiding estimating calories advantageously aids in improving the quality of diet since calorie estimation may be prone to error and, e.g., calorie counting may be less effective for weight loss and overall health than macronutrients composition balancing.

Figure 5B:
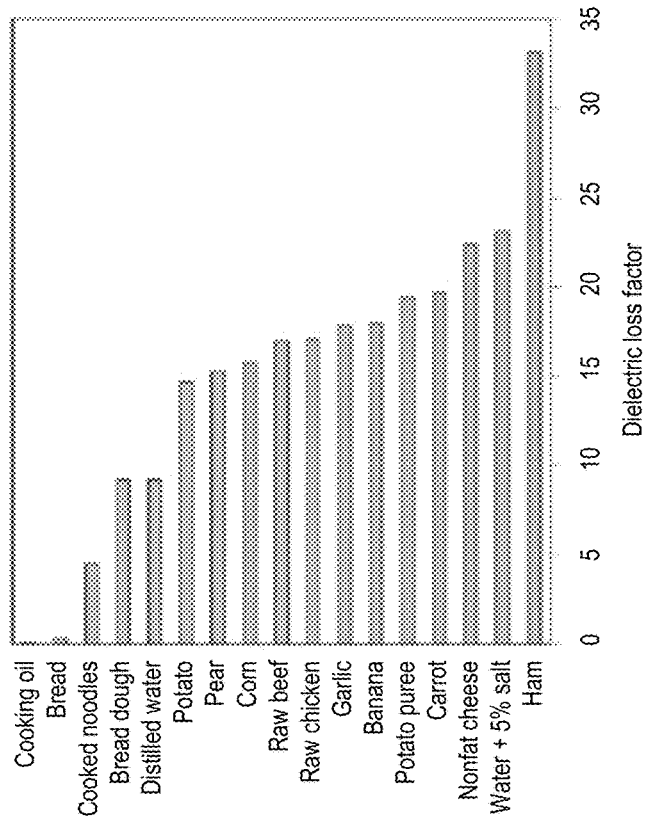
FIGS. 5A and 5B show dielectric constants and dielectric loss factor, respectively, of various food materials at 25° C.
Figure 5A:
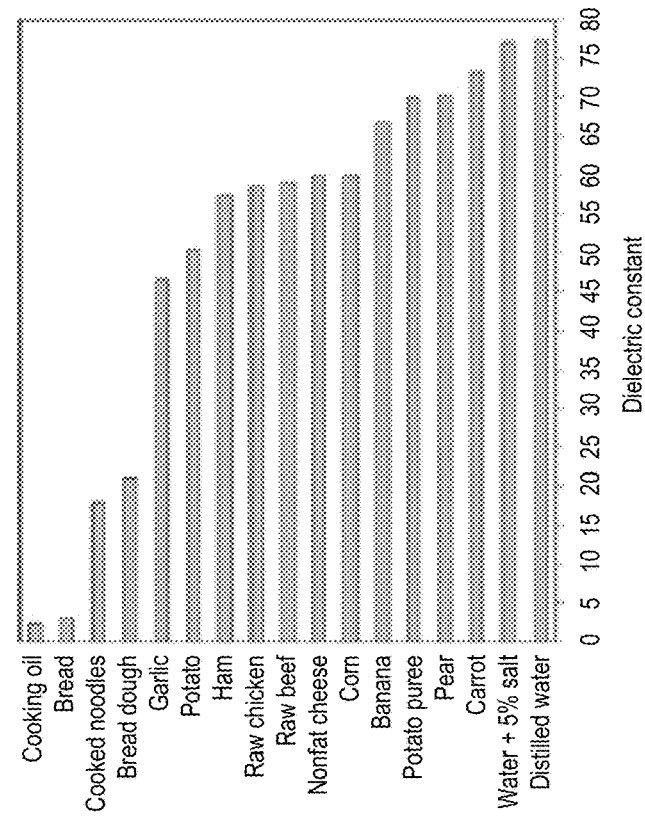

In some embodiments, a millimeter-wave radar is used to distinguish, e.g., between vegetables, fruits, grains, proteins, fats, and beverage types. For example, radar reflections are affected by the dielectric properties of a material, among other factors. Thus, in some embodiments, a millimeter-wave radar is used to distinguish between types of foods (e.g., between vegetables, fruits, grains, proteins, fats, and beverage types) based on signatures of the different radar reflections caused by different dielectric properties of the different foods. FIGS. 5A and 5B show dielectric constants and dielectric loss factor, respectively, of various food materials at 25° C.

In some embodiments, a millimeter-wave radar may be used at different frequencies (radar spectroscopy) to analyze food composition and quality. For example, in some embodiments, a millimeter-wave radar is used to estimate the sugar content in a yogurt or beverage.

In some embodiments, a 2D RGB camera may be used to augment the system's accuracy using image recognition. For example, in some embodiments, image recognition provides a secondary source of data to fuse with the radar data in food type recognition. In some embodiments, image recognition may be used for separating different piles of food in the images, as well as for separating the food from the background in the image.

In an embodiment, a smartphone includes a back-facing camera, a 3D imaging sensor, and a millimeter-wave radar. The 3D imaging sensor is implemented with a ToF sensor, e.g., in combination with the back-facing camera. The ToF sensor and the millimeter-wave radar, and optionally the back-facing camera, are used in conjunction to classify food based on their macronutrients composition. Other implementations are also possible. For example, some embodiments may implement the 3D imaging sensor for generating the 3D image using a Lidar of a phone.

Figure 6:
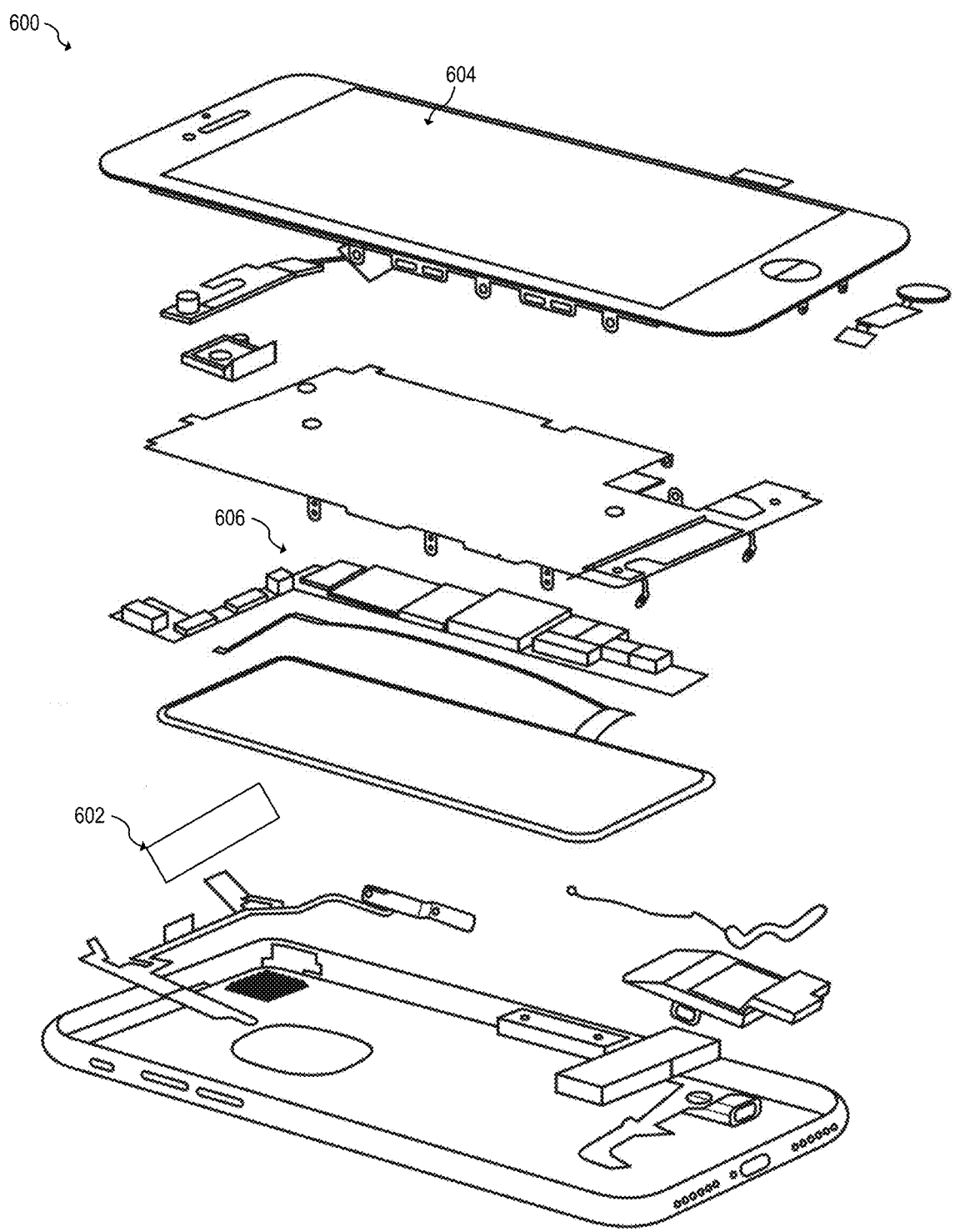
FIG. 6 shows a smartphone, according to an embodiment of the present invention.

FIG. 6 shows smartphone 600, according to an embodiment of the present invention. Smartphone 600 includes sensor module 602, touchscreen 604, and processor 606. Sensor module 602 includes a back-facing camera 712, a ToF sensor 714, and a millimeter-wave radar 716.

Some embodiments may be implemented in form factors different than a smartphone. For example, some embodiments may be implemented in head-mounted computing devices, such as augmented reality glasses. Some embodiments may be implemented in kiosks in a cafeteria or restaurants, e.g., such as a restaurant with self-serving buffet bars. Some embodiments may be implemented in specialized consumer devices, such as a home appliance that analyzes food, such as a smart scale or smart microwave. Other implementations are possible.

As shown in e.g., FIG. 6, some embodiments implement the 3D imaging sensor with a ToF sensor. Some embodiments implement the 3D imaging sensor in other ways. For example, some embodiments may use, instead of or in addition to the ToF sensor, ultrasonic sensors, multiple RGB cameras, an array of radar sensors, and/or Lidar sensor to implement the 3D imaging sensor.

In some embodiments, the radar may be substituted or augmented by using other sensors, such as ultrasonic spectrometers, hyperspectral imagers, or NIR spectrometers. For example, in some embodiments, an ultrasonic sensor is used to visualize the internal composition of a food (e.g., measure the thickness of a layer of fat on meat or detect the presence of chunky food in soups). In some embodiments, a hyperspectral imager is used to detect impurities or spoilage.

Touchscreen 604, RGB camera 712, and ToF sensor 714 may be implemented in any way known in the art. In some embodiments, the combination of RGB camera 712 and ToF sensor 714 may be operate as a 3D imaging sensor 711.

Processor 606 may be implemented in any way known in the art, such as a general purpose or custom processor, controller or digital signal processor (DSP) that includes, for example, combinatorial circuits coupled to a memory. In some embodiments, processor 1120 may include an artificial intelligence (AI) accelerator.

In some embodiments, processor 606 is configured to run an operating system of the smartphone 600, run apps, control peripherals (e.g., RGB camera 712, ToF sensor 714 and millimeter-wave radar 716) and/or perform other tasks associated with smartphone 600.

Figure 7:
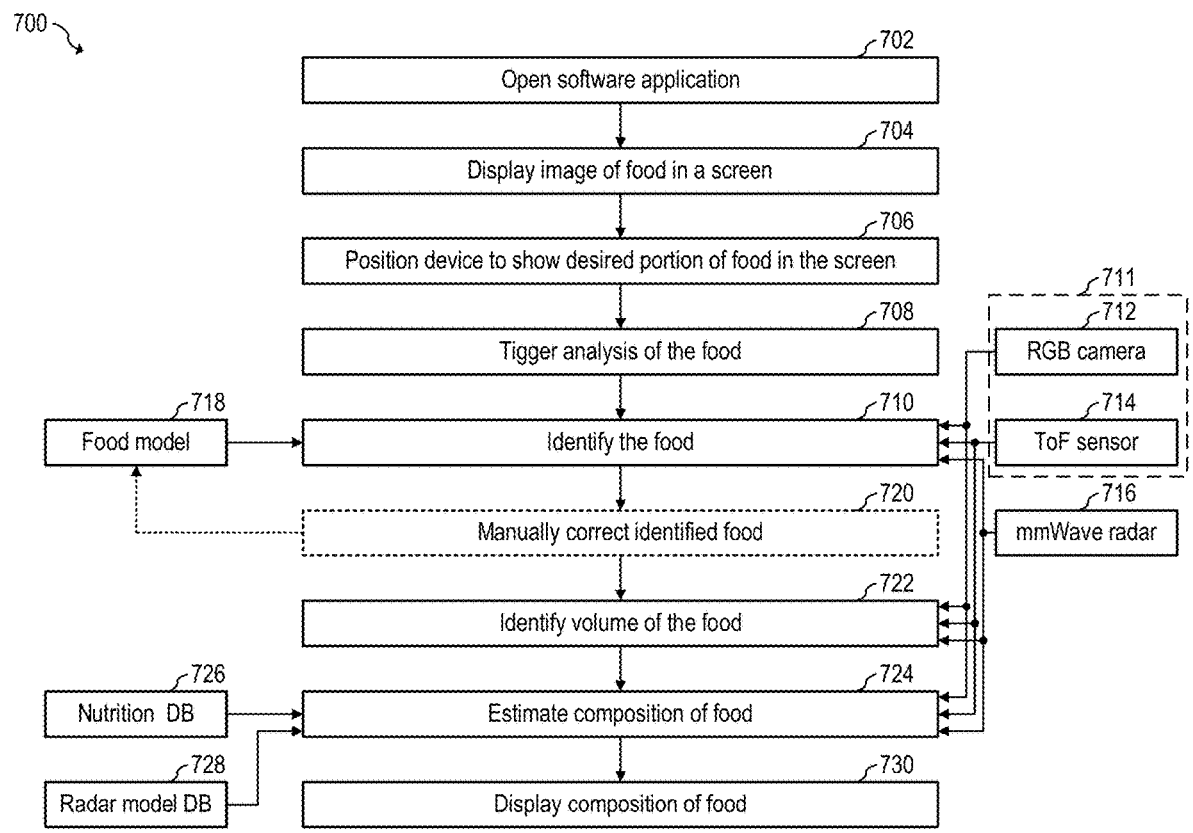
FIG. 7 shows a flow chart of an embodiment method for classifying food, according to an embodiment of the present invention.

FIG. 7 shows a flow chart of embodiment method 700 for classifying food, according to an embodiment of the present invention. The description of method 700 assumes an implementation with smartphone 600. It is understood that method 700 may be implemented in other types of devices.

During step 702, a user, such as a human, opens an app in smartphone 600, the app having system-level permission to access one or more sensors of sensor module 602. During step 704, the software application displays food in screen 604 using, e.g., the back-facing RGB camera 712 of smartphone 600.

During step 706, the user positions smartphone 600 so that the desired portion of the food (e.g., the entire portion of food to be analyzed) is shown in screen 604.

During step 708, the user triggers analysis of the food displayed in the screen 604, e.g., by touching a button of smartphone 600, such as by clicking in a virtual button displayed in touchscreen 604.

During step 710, the app uses one or more sensors of smartphone 600 to identify the food displayed in the screen 604. For example, in some embodiments, the back-facing RGB camera 712 of smartphone 600 is used to identify the food using conventional image recognition algorithms. For example, in some embodiments, a deep learning algorithm, such as AlexNet, ResNet, SqueezeNet, or DenseNet, may be used.

In some embodiments, the millimeter-wave radar 716 of smartphone 600 is used to identify the food. For example, in some embodiments, millimeter-wave radar 716 is used to generate 2D radar images. A neural network, such as a deep convolutional neural network (DCNN), may be used in conjunction with radar signal processing (e.g., MTI filtering, range FFT and Doppler FFT) to classify the food.

In some embodiments, the ToF sensor 714 of smartphone 600 is used to identify the food. For example, in some embodiments, depth distortion generated based on ToF data is used to distinguish between the background (e.g., table, plate, bowl, eating utensils, etc.) and the food.

In some embodiments, more than one sensor (e.g., two or more of ToF sensor 714, millimeter-wave radar 716, or RGB camera 712) may be combined to identify the food. For example, in some embodiments, objects in the field-of-view (FoV) of the sensors 712, 714, and 716 are segmented based on data from ToF sensor 714, millimeter-wave radar 716, and RGB camera 712 to identify individual objects. For example, in an embodiment, an image of a burger may be segmented, e.g., into table, plate, top half of the hamburger bun, tomatoes, lettuce, cheese, meat, and bottom half of the hamburger bun, where the identified food includes the top and bottom half of the hamburger bun, the tomatoes, the lettuce, the cheese, and meat, and the non-food includes the table and the plate. For example, in some embodiments, depth distortion (from ToF sensor 714) is used in relation to the image generated by RGB camera 712 to identify objects of different materials.

In some embodiments, the identification step 710 is based on food model 718. Food model 718 may be implemented with, e.g., a neural network (e.g., such as a DCNN), to differentiate between different food and non-food. The food model may be trained, e.g., during a characterization step (not shown), in which a training dataset that includes pre-labeled data associated with food and non-food is used to optimize the food model based on the output of one or more sensors (e.g., ToF sensor 714, millimeter-wave radar 716, and/or RGB camera 712).

In some embodiments, food model 718 may be stored in non-volatile memory of smartphone 600.

Figure 8:
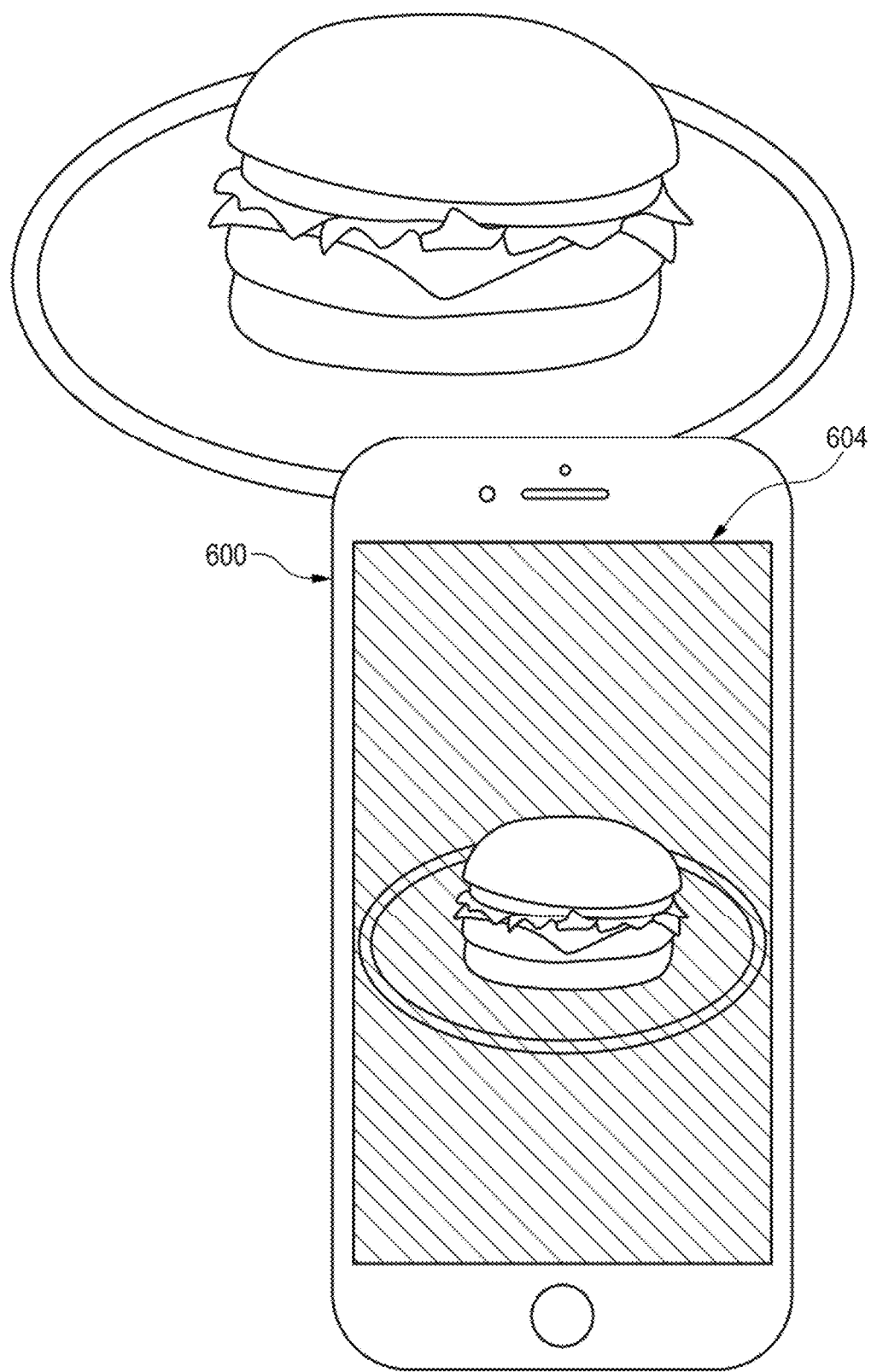
FIG. 8 shows a screen of the smartphone of FIG. 6 while displaying a burger, according to an embodiment of the present invention.

In some embodiments, the image displayed on the screen 604 may be modified as a result of the food identification step. For example, in some embodiments, portions of the image that are not food may be grayed out or dimmed. For example, FIG. 8 shows the screen 604 of smartphone 600 while displaying a burger, in which areas of the screen 604 that are not displaying food are grayed out, according to an embodiment of the present invention.

During step 720, the user may manually correct the results of the food identification step (step 710). For example, in some embodiments, the user may click on the touchscreen 604 to associate a portion of the screen 604 to food or non-food. In some embodiments, the characteristics of corrected objects may be used to further refine the food model.

During step 722, ToF sensor 714 is used to identify the volume of the identified food (e.g., identified during step 710), e.g., by generating a depth map and associating it with the segmented image. For example, a 2D image generated by RGB camera 712 may be associated with ToF data (e.g., a depth map) generated by ToF sensor 714 to generate a 3D image. The volume may be identified from the 3D image.

In some embodiments, the 3D image is processed separately, as a 2D image from RGB camera 712 and a depth map from ToF sensor 714 without creating a 3D image file (e.g., by associating points of the depth map with corresponding points of the 2D image without combining the 2D image and the depth map into the same file). For example, in some embodiments, the volume of the food is identified from the 3D image by segmenting the 2D image, associating points of the depth map to the segmented image, and determining the volume of the food based on the ToF data associated with the segmented image (e.g., without creating a 3D image file).

In some embodiments, the 2D image from RGB camera 712 and the depth map from ToF sensor are captured simultaneously. In some embodiments, the 2D image from RGB camera 712 and the depth map from ToF sensor are captured at different times. In some embodiments, the 3D image includes the merged data from the 2D image from RGB camera 712 and from the depth map from ToF sensor 714. In some embodiments, the 3D image is rendered in touchscreen 604. In some embodiments, the 3D image is used without displaying the 3D image in a screen.

During step 724, the composition of the identified food is determined. For example, in some embodiments, RGB camera 712 and/or ToF data from ToF sensor 714 is used to classify the identified food (e.g., an apple). The application then consults nutrition database 726 (e.g., in the cloud and/or stored locally in smartphone 600 in an app database) to infer the (generic) composition (e.g., the macronutrients) of the classified food.

In some embodiments, during step 724, millimeter-wave radar 716 extracts a food composition signature of the food (e.g., a measurement vector y, such as explained in more detailed below, e.g., with respect to FIGS. 13A and 13B and Equations 7 and 10) and compares such signature with radar model database 728 to identify a specific composition of the identified food. For example, in some embodiments, radar model database 728 holds models for each type of classified food (e.g., potato, pear, corn, etc.). In some embodiments, for each type of classified food, a radar signature has been computed for known compositions. For example, a model for apples holds signatures for apples of different ripeness and sugar levels. Similarly, a model for french fries holds signatures for french fries of varying fat levels and potato types. Once the particular type of food has been identified (e.g., an apple of a particular ripeness and sugar level), nutrition database 726 may be consulted to identify the specific composition (e.g., macronutrients) of the identified food.

In some embodiments, classification of different types of food displayed on the screen 604 (e.g., different types of food on a plate) is performed (e.g., sequentially or simultaneously). For example, a plate filled with pasta on a first half, and salad on a second half may first classify the pasta (e.g., by consulting databases 726 and 728 based on the output of sensors 712, 714 and 716 associated to the region of the screen 604 displaying the pasta), and then the salad (e.g., by consulting databases 726 and 728 based on the output of sensors 712, 714 and 716 associated to the region of the screen 604 displaying the salad).

In some embodiments, databases 726 and 728 may be stored in non-volatile memory of smartphone 600.

During step 730, the composition of the food estimated during step 724 is displayed. For example, FIGS. 9 and 10 show examples of possible ways to display the composition of the food estimated during step 724, according to embodiments of the present invention.

Figure 9:
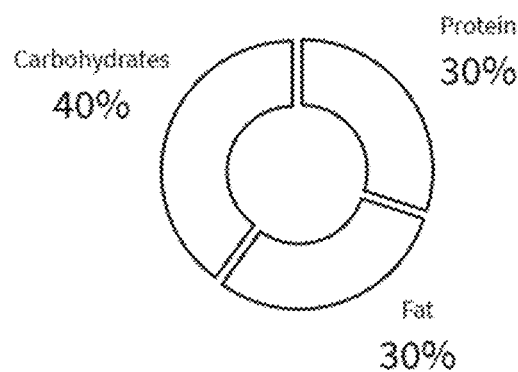
FIGS. 9 and 10 show examples of possible ways to display the composition of the food estimated while performing the method of FIG. 7, according to embodiments of the present invention.

As shown in FIG. 9, in some embodiments, the composition of may include a macronutrient composition of the food.

Figure 10:
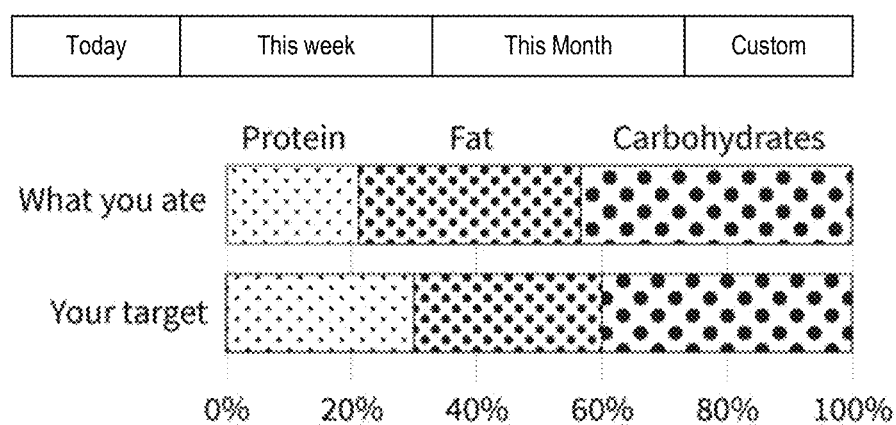

As shown in FIG. 10, in some embodiments, the composition of the food estimated during step 724 may be recorded and tracked, and may be displayed, e.g., by day, week, or month, or by a custom timeframe, for example. In some embodiments, the food composition history may be stored in a memory of smartphone 600. In some embodiments, the history of food composition intake may be used, e.g., as the basis to provide dietary suggestions.

In some embodiments, the smartphone app may provide suggestions for the user's next meal, e.g., to balance their macronutrient profile or meet their dietary goals, such as eating an extra serving of vegetables or protein.

In some embodiments, the smartphone app tracks the user's diet and may correlate diet with other information, such as weight, blood sugar, cholesterol, exercise/activity level, sleep, or pain level, e.g., depending on the user's goals.

In some embodiments, the smartphone app may suggest modifications to the user's dietary goals.

Figure 11:
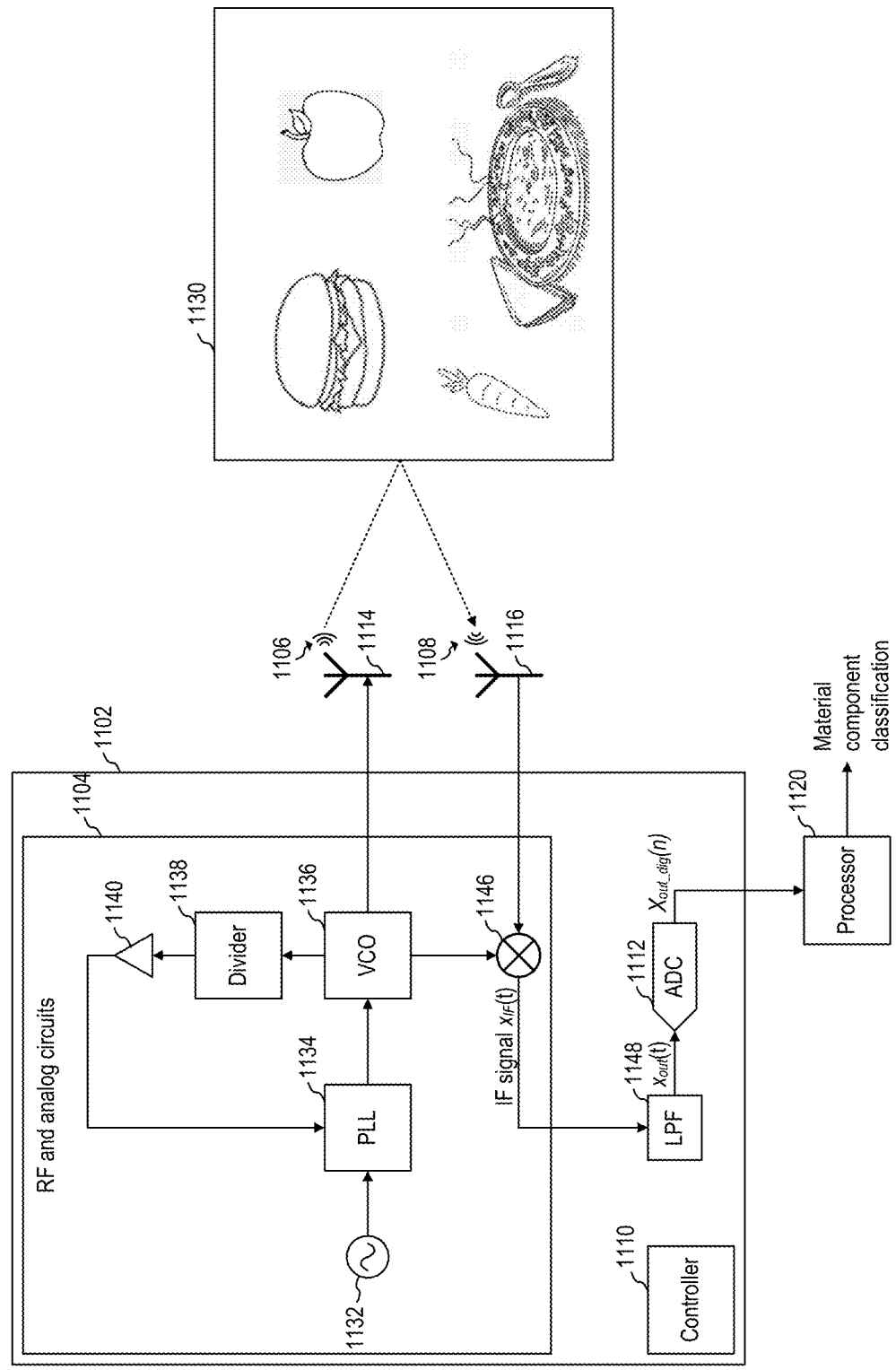
FIG. 11 shows a schematic diagram of the millimeter-wave radar of FIG. 7, according to an embodiment of the present invention.

Some embodiments may advantageously be used for treatments and/or prevention of obesity, heart disease, cancer, diabetes, and/or other chronic health problems. Some embodiments may be used to promote wellness (e.g., weight loss). In some embodiments, material component identification is performed by a millimeter-wave radar (e.g., 716) configured to perform minimum variance distortionless response (MVDR), also known as Capon, beamforming. For example, FIG. 11 shows a schematic diagram of millimeter-wave radar 716, according to an embodiment of the present invention.

During normal operation, millimeter-wave radar sensor 1102 operates as a frequency-modulated continuous-wave (FMCW) radar sensor and transmits a plurality of radar signals 1106, such as chirps, towards scene 1130 using transmitter (TX) antenna 1114. The radar signals 1106 are generated using RF and analog circuits 1104. The radar signals 1106 may be in the 20 GHz to 122 GHz range.

The objects in scene 1130 may include food, such as single items of food, such as a carrot or an apple, combination of food items, such as a burger, and non-food items, such as plates, silverware, and napkins, for example. Other objects may also be present in scene 1130, such as walls, countertops, furniture, etc.

The transmitted radar signals 1106 are reflected by objects in scene 1130. The reflected radar signals 1108, which are also referred to as the echo signal, are received by receiver (RX) antenna 1116. RF and analog circuits 1104 processes the received reflected radar signals 1108 using, e.g., bandpass filters (BPFs), low-pass filters (LPFs), mixers, low-noise amplifier (LNA), and/or intermediate frequency (IF) amplifiers in ways known in the art to generate an analog signal $x_{out}(t)$.

The analog signal $x_{out}(t)$ is converted to raw digital data $x_{out\_dig}(n)$ using ADC 1112. The raw digital data $x_{out\_dig}(n)$ is processed by processor 1120 to identify and classify the food components present in scene 1130.

Controller 1110 controls one or more circuits of millimeter-wave radar sensor 1102, such as RF and analog circuit 1104 and/or ADC 1112. Controller 1110 may be implemented as a custom or general purposes controller or processor, that includes, e.g., combinatorial circuits coupled to a memory.

Processor 1120 may be implemented in any way known in the art, such as a general purpose or custom processor, controller or digital signal processor (DSP) that includes, for example, combinatorial circuits coupled to a memory. In some embodiments, processor 1120 may include an artificial intelligence (AI) accelerator. In some embodiments, processor 1120 may be implement a portion of controller 1110. In some embodiments, a portion of processor 1120 may be implemented by processor 606.

RF and analog circuits 1104 may be implemented, e.g., as shown in FIG. 11. During normal operation, VCO 1136 generates a linear frequency chirp (e.g., from 57 GHz to 64 GHz), which is transmitted by transmitting antenna 1114. The VCO 1136 is controlled by PLL 1134, which receives a reference clock signal (e.g., 80 MHz) from reference oscillator 1132. PLL 1134 is controlled by a loop that includes frequency divider 1138 and amplifier 1140.

The linear chirp transmitted by transmitting antenna 1114 is reflected by objects in scene 1130 and received by receiving antenna 1116. The echo received by transmitting antenna 1116 is mixed with a replica of the signal transmitted by transmitting antenna 1114 using mixer 1146 to reduce an intermediate frequency (IF) signal $x_{IF}(t)$ (also known as the beat signal). In some embodiments, the beat signal $x_{IF}(t)$ has a bandwidth between 10 kHz and 1 MHz. A beat signal $x_{IF}(t)$ with a bandwidth lower than 10 kHz or higher than 1 MHz is also possible.

The beat signal $x_{IF}(t)$ is filtered with low-pass filter (LPF) 1148 and then sampled by ADC 1112. ADC 1112 is advantageously capable of sampling the filtered beat signal $x_{out}(t)$ with a sampling frequency that is much smaller than the frequency of the signal received by receiving antenna 1116. Using FMCW radars, therefore, advantageously allows for a compact and low cost implementation of ADC 1112, in some embodiments.

The raw digital data $x_{out\_dig}(n)$, which in some embodiments is the digitized version of the filtered beat signal $x_{out}(t)$, is (e.g., temporarily) stored (e.g., in matrices of $N_c \times N_s$, where $N_c$ is the number of chirps considered in a frame and $N_s$ is the number of transmit samples per chirp) for further processing.

In some embodiments, ADC 1112 is a 12-bit ADC. ADCs with higher resolution, such as 14-bits or higher, or with lower resolution, such as 10-bits, or lower, may also be used.

FIG. 12 shows a block diagram of embodiment method 1200 for performing food classification (step 724) using millimeter-wave radar 716, according to an embodiment of the present invention.

During step 1202, raw ADC data $x_{out\_dig}(n)$ is received. The raw ADC data $x_{out\_dig}(n)$ includes separate baseband radar data from multiple antennas 1116. During step 1202, signal conditioning, low pass filtering and background removal is performed on the raw ADC data $x_{out\_dig}(n)$. For example, in some embodiments, the raw ADC data $x_{out\_dig}(n)$ are filtered, DC components are removed to, e.g., remove the Tx-Rx self-interference and optionally pre-filtering the interference colored noise. In some embodiments, filtering includes removing data outliers that have significantly different values from other neighboring range-gate measurements. Thus, this filtering also serves to remove background noise from the radar data. For example, in some embodiments, a Hampel filter is applied with a sliding window at each range-gate to remove such outliers. Alternatively, other filtering for range preprocessing known in the art may be used.

During step 1204, a series of FFTs are performed on conditioned radar data $X_{conditioned}(n)$ produced during step 1202. In some embodiments, a windowed FFT having a length of the chirp (e.g., 256 samples) is calculated along each waveform for each of a predetermined number of chirps in a frame of data. Alternatively, other frame lengths may be used. The FFTs of each waveform or chirp may be referred to as a "range FFT." In alternative embodiments, other transform types could be used besides an FFT, such as a Discrete Fourier Transform (DFT) or a z-transform.

During step 1206, capon beamforming is performed. A beam is formed at the transmitter by post processing a plurality of baseband signals based on a plurality of signals received by different receivers (e.g., different RX antennas 1116) or a combination thereof. Implementing beamforming by post processing received baseband signals may allow for the implementation of a low complexity transmitter.

In some embodiments, millimeter-wave radar 716 includes $N_t=2$ transmit (TX) elements and $N_r=2$ receive (RX) elements arranged in an array. Accordingly, there are $N_t \times N_r=4$ distinct propagation channels from the TX array to the RX array in an array configuration for azimuth angle profiling. If the transmitting source (TX channel) of the received signals can be identified at the RX array, a virtual phased array of $N_t \times N_r$ elements can be synthesized with $N_t+N_r$ antenna elements. In various embodiments, a time division multiplexed MIMO array provides a low cost solution to a fully populated antenna aperture capable of near field imaging.

The transmitter steering vector may be expressed as $$a_m^{Tx}(\theta) = e^{-j2\pi \cdot \frac{d_m^{Tx} \cdot \sin(\theta)}{\lambda}} \quad (1)$$

where $\theta$ is the angle of the target (e.g., the angle pointing towards the location where the food), $\lambda$ is the wavelength of the transmitted signal (e.g., the center frequency of the chirp), $d_m^{Tx}$ is the positional vector of the $m^{th}$ transmitting antenna with respect to the center of the transmitting antenna array, and m=1, 2 (for each of the TX antennas).

The receiver steering vector may be expressed as $$a_m^{Rx}(\theta) = e^{-j2\pi \cdot \frac{d_m^{Rx} \cdot \sin(\theta)}{\lambda}} \quad (2)$$

where $d_n^{Tx}$ is the positional vector of $n^{th}$ receiving antenna with respect to the center of the receiving antenna array, and n=1, 2 (for each of the RX antennas).

In some embodiments, the azimuth imaging profile for range bin l is generated using the Capon spectrum from the beamformer. The Capon beamformer is computed by minimizing the variance/power of noise while maintaining a distortion-less response towards a desired angle. The corresponding quadratic optimization problem can be expressed as $$\min_w w^H C w \text{ s.t. } w^H(a^{Tx}(\theta) \otimes a^{Rx}(\theta)) = 1 \qquad (3)$$

where w represent the beamforming weights for the particular angle θ (where the constraint function is ensuring unit response), and C is the covariance matrix of noise.

Equation 3 is an optimization that has a closed form expression that may be given by $$w_{capon} = C^{-1} \cdot \frac{a(\theta)}{a^H(\theta) C^{-1} a(\theta)}. \qquad (4)$$

The spatial spectrum, thus, may be given by $$P_l(\theta) = \frac{1}{(a^{Tx}(\theta) \otimes a^{Rx}(\theta))^H C_l^{-1} (a^{Tx}(\theta) \otimes a^{Rx}(\theta))} \qquad (5)$$

where l=0, . . . , L, L being the total number of range bins.

In some embodiments, $C_l$ is estimated instead of the noise covariance matrix C. $C_l$ is the estimated covariance matrix based on the range data at range bin l (e.g., if the virtual antenna has a dimension 8, $C_l$ is a matrix is 8×8 for each range bin). $C_l$ includes the signal component (similarly than noise covariance matrix C) and can be estimated using sample matrix inversion (SMI) technique. In some embodiments, estimating $C_l$ may be simpler than estimating the noise covariance matrix C. $C_l$ may be estimated by $$C_l = \frac{1}{N} \sum_{k=1}^{K} s_l^{IF}(k) s_l^{IF}(k)^H \qquad (6)$$

where K represents the number of snapshots, and $s_l^{IF}(k)$ represents the received signal at $l^{th}$ range bin at $k^{th}$ measurement. In some embodiments, the snapshot could represent the chirp number or frame number based on which data is used to update the covariance matrix.

During step 1208, the discrete cosine transform (DCT) is performed. In some embodiments, step 1208 advantageously allows for achieving dimensionality reduction. In some embodiments, step 1208 may be omitted.

During step 1210, sparse decomposition (with dictionary learning) is performed. Step 1210 may be understood in view of FIGS. 13A and 13B. FIGS. 13A and 13B illustrate possible embodiments for performing step 1210, according to an embodiment of the present invention. In some embodiments, the representation illustrated in FIG. 13B corresponds to performing step 1210 directly from the output of step 1206 (omitting step 1208).

Figure 13A:
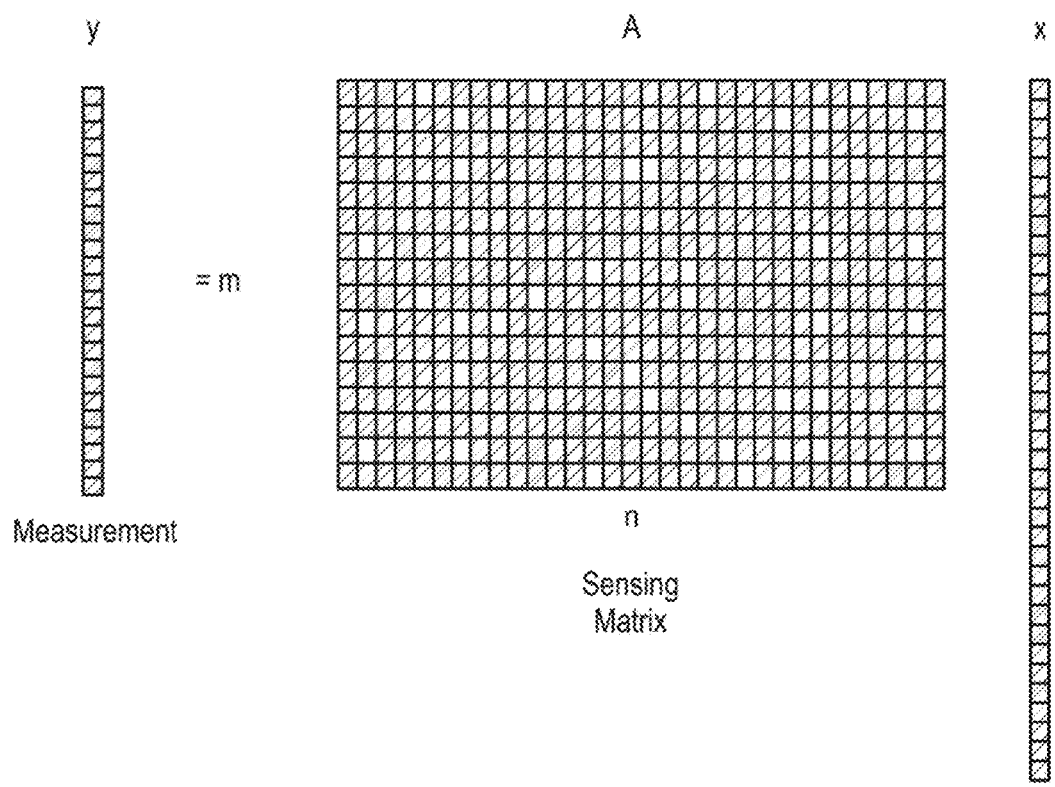
FIGS. 13A and 13B illustrate possible embodiments for performing a portion of the method of FIG. 12, according to embodiments of the present invention.

As shown in FIG. 13A, the sensing equation may be given by $$y = Ax \qquad (7)$$

where y is the measurement vector (e.g., measurements performed by millimeter-wave radar 716, such as measurements at the output of step 1208), A is the sensing matrix, where A has dimensions of m×n, (where each column of A corresponds to a radar signature of a type of food) and x is a vector including the food composition to be identified (e.g., where each cell (row) of the vector x corresponds to a particular food type (column of matrix A)). In some embodiments, matrix A may be stored in radar model database 728.

Since there is only one measurement vector y and there are several unknown components (food composition) to be identified, the problem is under-determined, which in a normal formulation entails infinite solutions. To avoid infinite solutions, the structure is forced to have a dictionary A, so each column of A represents a component and x is either 0 or 1, indicating whether that component is present in the measurement vector y or not. For example, matrix A may be understood as a learned dictionary, in which each column corresponds to a signature of a type of food (e.g., potato, pear, corn, etc.) and each row of each column (e.g., each cell of the column) corresponds to a range-azimuth (and optionally angle) collapsed into a single vector (e.g., as a result of performing a vectorization operation).

Matrix A may be generated by characterizing hundreds or thousands of different types of foods (e.g., potato, pear, corn, etc.). For example, in some embodiments, matrix A may be generated by collecting radar measurements (e.g., such as measurements at the output of step 1208 or step 1206) of different types of foods (e.g., potato, pear, corn, etc.), where the measurements of each type of food is arranged in respective columns of matrix A.

Various approximation (also referred to as pursuit) algorithms may be used to address the sparse representation problem. For example, in some embodiments, $$\min_{s \in R^P} |s|_o \text{ s.t.} |y - As|_2^2 \leq \varepsilon \qquad (8)$$

where p represents the number of components in the sensed image, $|\cdot|_0$ denotes a Lo norm.

In some embodiments, since the problem is NP-Hard, it may be approximated as $$\min_{s \in R^P} |s|_1 + \lambda |y - As|_2^2 \qquad (9)$$

where $|\cdot|_1$ denotes a L1 norm and $|\cdot|_2$ denotes a L2 norm.

In some embodiments, matching pursuit (MP) is used to solve the optimization problem of Equation 9. Matching pursuit may be understood as a greedy iterative algorithm that gradually finds the locations of the non-zeros in x one at a time. In each step, the MP algorithm finds the column in A that best correlates with the current residual, and then updates this residual to take the new component and its coefficient into account. Matching pursuit might pick the same atom multiple times.

In some embodiments, orthogonal matching pursuit is used to solve the optimization problem of Equation 9. Orthogonal matching pursuit operates in a similar manner as MP. In orthogonal matching pursuit, however, all the non-zero coefficients are updated by a Least-Squares in each of the algorithm's step. As a consequence, the residual is orthogonal to the already chosen component, and thus an atom cannot be picked more than once.

After solving Equation 7, e.g., using optimization techniques, vector x is obtained. In some embodiments, each cell of vector x corresponds to a particular types of foods (e.g., potato, pear, corn, etc.) and includes a number between 0 and 1, such as 0, or 1. An additional thresholding step (e.g., rounding) may be performed to obtain a vector x with only 0 and 1. Cells of vector x having 1 are indicative of the corresponding food being present in the measured food (as reflected by vector y) while cells having a o are indicative of the corresponding food not being present in the measured food. In other words, in some embodiments, after solving for x in Equation 7, the combination of foods (columns of matrix A) that better approximate the measurement vector y are indicated by the cells labeled as 1 in vector x. Thus, in some embodiments performing step 1210 in accordance with the embodiment of FIG. 13A, the material component classification obtained as the output of step 1210 may be a classification of types of food (e.g., potato, pear, corn, etc.).

Figure 13B:
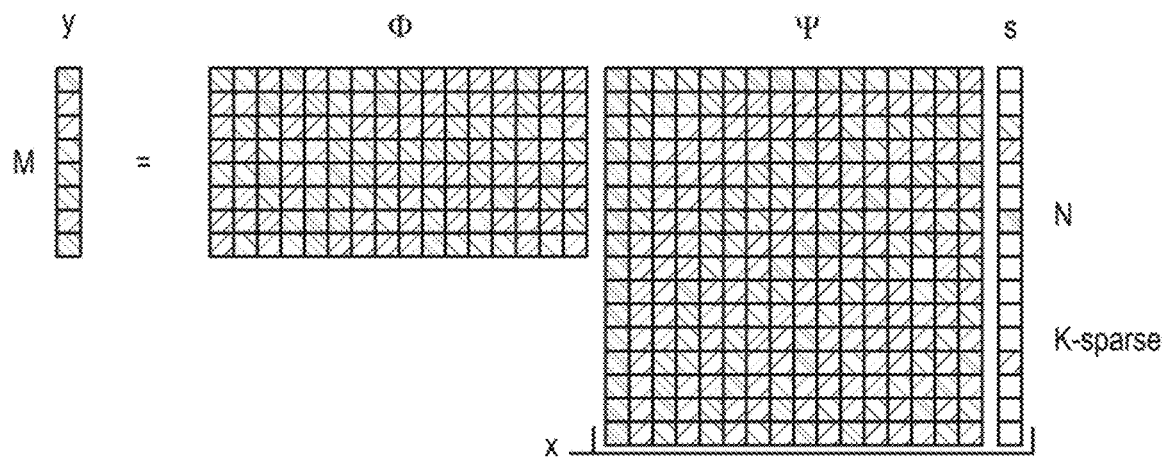

As shown in FIG. 13B, the sensing equation may be given by $$y = \Phi \Psi s \qquad (10)$$

where y is the measurement vector (e.g., measurements performed by millimeter-wave radar 716, such as measurements at the output of step 1206), $\psi$ is a first sensing matrix (e.g., similar or identical to sensing matrix A, $\Phi$ is a second sensing matrix, and s is a vector including the food composition to be identified. In some embodiments, matrices $\psi$ and $\Phi$ may be stored in radar model database 728.

In some embodiments in which step 1208 is omitted, Matrix $\Phi$ may be understood as a learned dictionary in which each column corresponds to a signature of a combination of 2 or more foods (e.g., 30% potato, 45% pear, and 25% corn) and each row of each column (e.g., each cell of the column) corresponds to a range-azimuth (and optionally angle) collapsed into a single vector (e.g., as a result of performing a vectorization operation).

Equation 10 may be solved for s using optimization techniques (e.g., matching pursuit). In some embodiments, the resulting vector s includes at most K non-zero cells (K-sparse), where K is a positive integer greater than 1, such as 8, 12, 13, or more. Each of the cells of vector s corresponds to a particular type of food (e.g., potato, pear, corn, etc.), and the value of each cell of s is indicative of the proportion of the associated type of food in the measurement vector y. For example, vector s may have, after solving Equation 10 for a particular measurement vector y, 3 non-zero cells corresponding to 3 types of foods (e.g., potato, pear, and corn), and the values of such 3 non-zero cells (e.g., 0.3, 0.45, 0.25) are indicative of the proportion of such foods in the measurement vector y (e.g., 30% potato, 45% pear, and 25% corn). Thus, in some embodiments performing step 1210 in accordance with the embodiment of FIG. 13B, the material component classification obtained as the output of step 1210 may be a classification of types and proportion of food (e.g., 30% potato, 45% pear, and 25% corn).

In some embodiments, an additional step may be performed after obtaining the types and proportion of foods to obtain the proportion of macronutrients associated with the measurement vector y (e.g., associated with the food being analyzed with the app in smartphone 600 (e.g., as illustrated in FIG. 8). For example, after determining that the food being analyzed includes (e.g., 30% potato, 45% pear, and 25% corn), a database (e.g., nutrition database 728) may be consulted to obtain the macronutrients (e.g., carbohydrates, proteins, fats, etc.) of the identified foods (e.g., potato, pear, and corn), and such macronutrients being multiplied by their proportions to arrive at a composition of macronutrients of the analyzed food). Such composition of macronutrients may be displayed, e.g., as illustrated in FIGS. 9 and/or 10, for example. Thus, in some embodiments performing step 1210 in accordance with the embodiment of FIG. 13B, the material component classification obtained as the output of step 1210 may be a classification of types and proportion of macronutrients (e.g., 30% carbohydrates, 45% protein, and 25% fat).

In some embodiments, the proportion of macronutrients obtained from the output of step 1210 may be combined with the volume of the food (e.g., identified during step 722) to determine the quantity of macronutrients.

FIG. 14 shows a block diagram of embodiment method 1400 for performing food classification (step 724) using millimeter-wave radar 716, according to an embodiment of the present invention. Method 1400 implements steps 1202, 1204, and 1206 in a similar manner as method 1200.

During step 1402, a DCNN is used to determine the composition of food based on the output from step 1206. The output of step 1402 may be, e.g., types of food present in the identified food (e.g., potato, pear, corn, etc.), types and proportion of food (e.g., 30% potato, 45% pear, and 25% corn) and/or types and proportion of macronutrients (e.g., 30% carbohydrates, 45% protein, and 25% fat).

In some embodiments, the DCNN used during step 1402 may be implemented with 5 residual convolutional layers with maxpooling, followed by 2 fully-connected layers, followed by a softmax output. Other implementations are also possible.

Figure 15:
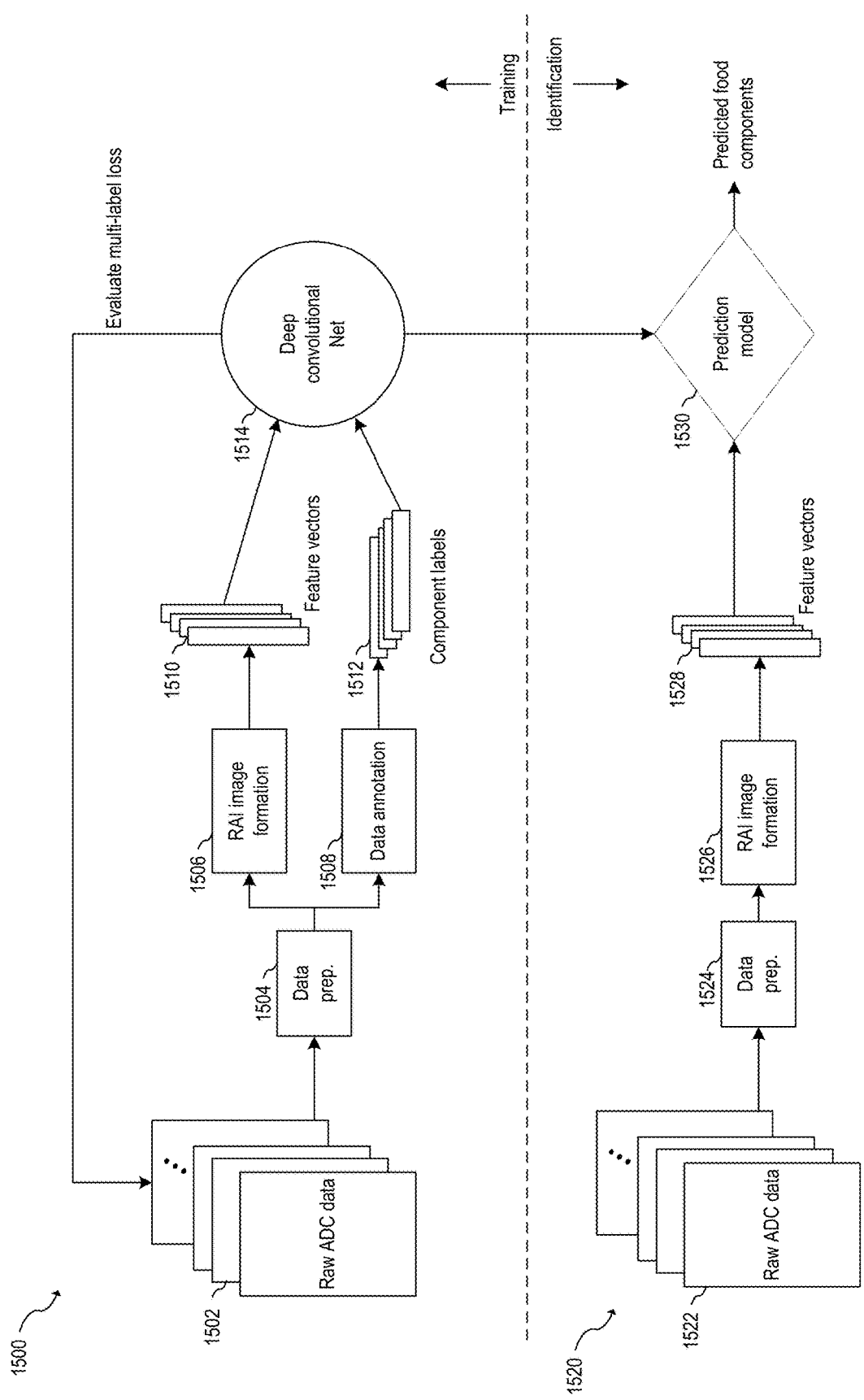
FIG. 15 illustrates a block diagram showing training and operation of a DCNN used during identification of food components, according to an embodiment of the present invention.

In some embodiments, the DCNN used during step 1402 may be trained using supervised training based on training data that includes sample foods and combination of foods. FIG. 15 illustrates a block diagram showing training and operation of a DCNN used during step 1402 for identification of food components, according to an embodiment of the present invention. The top portion 1500 of FIG. 15 illustrates the training of the DCNN, while the bottom portion 1520 of FIG. 15 illustrates the trained DCNN during normal operation.

During training, radar ADC data 1502, e.g., from ADC 1112, (also referred to as training data 1502), is transformed into feature vectors 1510 and corresponding component labels 1512. Feature vectors 1510 represent sets of generated vectors that are representative of training data 1502. The feature vectors 1510 are generated by a data preparation step 1504 (e.g., steps 1202 and 1204), and a range-angle image (RAI) formation step (e.g., step 1206).

Component labels 1512 represent user metadata associated with the corresponding training data 1502 and feature vectors 1510 (and corresponding to the dictionary vectors in step 1210, such as in matrices A, $\psi$ and $\Phi$). Component labels 1512 are generated by a data annotation step 1508, in which metadata is generated to identify the food components present in the training data set. For example, if a sample of training data 1502 corresponds to a particular carrot, the component label associated with the corresponding feature vector includes the components of such particular carrot.

The featured vectors 1510 and corresponding component labels 1512 are fed into the DCNN optimization algorithm 1514. The DCNN optimization algorithm 1514 optimizes the weights of the DCNN to minimize the multi-label loss.

During the optimization process, multiple samples, such as thousands of samples are used to train the DCNN. The trained DCNN is the prediction model 1530 used to predict food components during normal operation.

The training performance of the DCNN optimization algorithm 1514 may be determined by calculating the cross-entropy performance. In some embodiments, the DCNN optimization algorithm 1514 iteratively adjusts image formation parameters, such as the number of snapshots, for a classification accuracy of at least 90%. Alternatively, other classification accuracies could be used.

In some embodiments, an RMSprop optimizer is used to optimize the DCNN. Other optimizers, such as a gradient decent optimizer, and gradient decent with momentum optimizer, ADAM, may also be used. In some embodiments, the learning rate is $l_r$ is 0.0001, with $\rho$ of 0.9 and $\varepsilon$ of $10^{-8}$. Other learning parameter values may also be used.

During normal operation, radar ADC data 1522, e.g., from ADC 1112, is prepared during step 1524 (e.g., steps 1202 and 1204), and featured vectors 1528 are generated during a RAI formation step (e.g., step 1206). Featured vectors 1528 are fed to the DCNN (prediction model) 1530 to generate the predicted composition of the food.

Example embodiments of the present invention are summarized here. Other embodiments can also be understood from the entirety of the specification and the claims filed herein.

Example 1. A method for estimating a composition of food, the method including: receiving a first 3D image; identifying food in the first 3D image; determining a volume of the identified food based on the first 3D image; and estimating a composition of the identified food using a millimeter-wave radar.

Example 2. The method of example 1, further including: receiving data from a 3D imaging sensor; and generating the first 3D image based on the data from the 3D imaging sensor.

Example 3. The method of one of examples 1 or 2, where a mobile device includes the 3D imaging sensor, the millimeter-wave radar, and a screen, the method further including: positioning the mobile device to display the food on the screen; and triggering food analysis after displaying the food on the screen, and before receiving the data from the 3D imaging sensor.

Example 4. The method of one of examples 1 to 3, further including opening an app in the mobile device before triggering the food analysis.

Example 5. The method of one of examples 1 to 4, further including: displaying a second image on a screen, the second image based on the first 3D image; and manually adjusting which portion of the screen corresponds to food based on a user input.

Example 6. The method of one of examples 1 to 5, where identifying the food includes using a food model, the method further including updating the food model based on the manually adjusting.

Example 7. The method of one of examples 1 to 6, further including displaying a second image on a screen, the second image based on the first 3D image, where displaying the second image on the screen includes graying out portions of the second image that correspond to non-food.

Example 8. The method of one of examples 1 to 7, further including displaying an estimated composition of the identified food on a screen.

Example 9. The method of one of examples 1 to 8, further including recording a history of food composition intake based on estimated food compositions; and displaying dietary suggestions based on the history of food composition intake.

Example 10. The method of one of examples 1 to 9, where identifying the food in the first 3D image includes segmenting the first 3D image based on outputs from the 3D imaging sensor and the millimeter-wave radar.

Example 11. The method of one of examples 1 to 10, where identifying food in the first 3D image includes using an image recognition algorithms.

Example 12. The method of one of examples 1 to 11, further including generating a 2D radar image with the millimeter-wave radar, where identifying food in the first 3D image includes using the 2D radar image.

Example 13. The method of one of examples 1 to 12, where estimating the composition of food includes: generating a food composition signature of the food using the millimeter-wave radar; providing a first classification of the food by comparing the food composition signature to a radar model database; and estimating the composition of the food based on the first classification and a nutrition database.

Example 14. The method of one of examples 1 to 13, where estimating the composition of food includes: receiving radar data from an ADC of the millimeter-wave radar; preprocessing the received radar data to generate a radar image; and using a deep convolutional neural network (DCNN) to estimate the composition of the food based on the radar image.

Example 15. The method of one of examples 1 to 14, where the radar image is a range-angle image (RAI).

Example 16. The method of one of examples 1 to 15, further including training the DCNN.

Example 17. The method of one of examples 1 to 16, where estimating the composition of food includes: receiving radar data from an ADC of the millimeter-wave radar; preprocessing the received radar data to generate a radar image; performing a discrete cosine transform on the radar image to generate a transformed output; and performing a sparse decomposition based on the transformed output to estimate the composition of the food.

Example 18. A mobile device including: a 3D imaging sensor configured to generate a first 3D image; a millimeter-wave radar configured to transmit radar signals and receive reflected radar signals; and a processor configured to: identify food in the first 3D image; determine a volume of the identified food based on the first 3D image; and estimate a composition of the identified food based on the reflected radar signals.

Example 19. The mobile device of example 18, where the 3D imaging sensor includes a time-of-flight sensor.

Example 20. The mobile device of one of examples 18 or 19, where the 3D imaging sensor further includes an RGB camera.

Example 21. The mobile device of one of examples 18 to 20, where the 3D imaging sensor includes a Lidar sensor.

Example 22. The mobile device of one of examples 18 to 21, where the mobile device is a smartphone.

Example 23. The mobile device of one of examples 18 to 22, further including a screen configured to display a second image that is based on the first 3D image.

Example 24. The mobile device of one of examples 18 to 23, where the processor is configured to determine a quantity of macronutrients of the identified food based on the determined volume and the estimated composition of the identified food.

Example 25. A system including: a time-of-flight sensor; a camera; and a millimeter-wave radar configured to transmit radar signals and receive reflected radar signals; and a processor configured to: identify food based on an output of the camera; determine a volume of the identified food based on an output of the time-of-flight sensor; estimate a composition of the identified food based on the reflected radar signals; and determine a quantity of macronutrients of the identified food based on the determined volume and the estimated composition of the identified food.

Example 26. The system of example 25, where the processor is further configured to generate a measurement vector based on the reflected radar signals, where estimating the composition of the identified food includes estimating the composition of the identified food based on the measurement vector and a first sensing matrix, the first sensing matrix including radar signatures of a plurality of types of food.

Example 27. The system of one of examples 25 or 26, where estimating the composition of the identified food is further based on a second sensing matrix, the second sensing matrix including radar signatures of combinations of 2 or more types of foods.

Example 28. A method for estimating a composition of food, the method including: receiving radar data from an ADC of a millimeter-wave radar; preprocessing the received radar data to generate a radar image; generating a measurement vector based on the radar image; and estimating a composition of food based on the measurement vector and a first sensing matrix, the first sensing matrix including radar signatures of a plurality of types of food.

Example 29. The method of example 28, where the estimated composition of food includes one or more types of food.

Example 30. The method of one of examples 28 or 29, where estimating the composition of food is further based on a second sensing matrix, the second sensing matrix including radar signatures of combinations of 2 or more types of foods.

Example 31. The method of one of examples 28 to 30, where the estimated composition of food includes proportions of fats, proteins, and carbohydrates.

While this invention has been described with reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:

1. A method for estimating a composition of food, the method comprising:
   receiving a first 3D image;
   identifying food in the first 3D image;
   determining a volume of the identified food based on the first 3D image; and
   estimating a composition of the identified food using a millimeter-wave radar, wherein estimating the composition of food comprises:
   receiving radar data from an ADC of the millimeter-wave radar,
   preprocessing the received radar data to generate a radar image, and
   using a deep convolutional neural network (DCNN) to estimate the composition of the food based on the radar image.

2. The method of claim 1, further comprising:
   receiving data from a 3D imaging sensor; and
   generating the first 3D image based on the data from the 3D imaging sensor.

3. The method of claim 2, wherein a mobile device comprises the 3D imaging sensor, the millimeter-wave radar, and a screen, the method further comprising:
   positioning the mobile device to display the food on the screen; and
   triggering food analysis after displaying the food on the screen, and before receiving the data from the 3D imaging sensor.

4. The method of claim 3, further comprising opening an app in the mobile device before triggering the food analysis.

5. The method of claim 1, further comprising:
   displaying a second image on a screen, the second image based on the first 3D image; and
   manually adjusting which portion of the screen corresponds to food based on a user input.

6. The method of claim 5, wherein identifying the food comprises using a food model, the method further comprising updating the food model based on the manually adjusting.

7. The method of claim 1, further comprising displaying a second image on a screen, the second image based on the first 3D image, wherein displaying the second image on the screen comprises graying out portions of the second image that correspond to non-food.

8. The method of claim 1, further comprising displaying an estimated composition of the identified food on a screen.

9. The method of claim 8, further comprising recording a history of food composition intake based on estimated food compositions; and
   displaying dietary suggestions based on the history of food composition intake.

10. The method of claim 2, wherein identifying the food in the first 3D image comprises segmenting the first 3D image based on outputs from the 3D imaging sensor and the millimeter-wave radar.

11. The method of claim 1, wherein identifying food in the first 3D image comprises using an image recognition algorithms.

12. The method of claim 1, further comprising generating a 2D radar image with the millimeter-wave radar, wherein identifying food in the first 3D image comprises using the 2D radar image.

13. The method of claim 1, wherein estimating the composition of food comprises:
   generating a food composition signature of the food using the millimeter-wave radar;
   providing a first classification of the food by comparing the food composition signature to a radar model database; and
   estimating the composition of the food based on the first classification and a nutrition database.

14. The method of claim 1, wherein the radar image is a range-angle image (RAI).

15. The method of claim 1, further comprising training the DCNN.

16. A method for estimating a composition of food, the method comprising:
   receiving a first 3D image;
   identifying food in the first 3D image;
   determining a volume of the identified food based on the first 3D image; and
   estimating a composition of the identified food using a millimeter-wave radar, wherein estimating the composition of food comprises:
   receiving radar data from an ADC of the millimeter-wave radar,
   preprocessing the received radar data to generate a radar image,
   performing a discrete cosine transform on the radar image to generate a transformed output, and
   performing a sparse decomposition based on the transformed output to estimate the composition of the food.

17. A mobile device comprising:
a 3D imaging sensor configured to generate a first 3D image;
a millimeter-wave radar configured to transmit radar signals and receive reflected radar signals; and
a processor configured to:
   identify food in the first 3D image;
   determine a volume of the identified food based on the first 3D image; and
   estimate a composition of the identified food based on the reflected radar signals, by receiving radar data from an ADC of the millimeter-wave radar,
      preprocessing the received radar data to generate a radar image, and
      using a deep convolutional neural network (DCNN) to estimate the composition of the food based on the radar image.

18. The mobile device of claim 17, wherein the 3D imaging sensor comprises a time-of-flight sensor.

19. The mobile device of claim 18, wherein the 3D imaging sensor further comprises an RGB camera.

20. The mobile device of claim 17, wherein the 3D imaging sensor comprises a Lidar sensor.

21. The mobile device of claim 17, wherein the mobile device is a smartphone.

22. The mobile device of claim 17, further comprising a screen configured to display a second image that is based on the first 3D image.

23. The mobile device of claim 17, wherein the processor is configured to determine a quantity of macronutrients of the identified food based on the determined volume and the estimated composition of the identified food.

24. A system comprising:
a time-of-flight sensor;
a camera; and
a millimeter-wave radar configured to transmit radar signals and receive reflected radar signals; and
a processor configured to:
   identify food based on an output of the camera;
   determine a volume of the identified food based on an output of the time-of-flight sensor;
   generate a measurement vector based on the reflected radar signals;
   estimate a composition of the identified food based on the reflected radar signals based on the measurement vector and a predetermined first sensing matrix, the first sensing matrix comprising radar signatures of a plurality of types of food, wherein each column of the first sensing matrix comprises a radar signature that corresponds to a particular type of food; and
   determine a quantity of macronutrients of the identified food based on the determined volume and the estimated composition of the identified food.

25. The system of claim 24, wherein the processor is further configured to estimate the composition of the food by:
   receiving radar data from an ADC of the millimeter-wave radar,
   preprocessing the received radar data to generate a radar image,
   performing a discrete cosine transform on the radar image to generate the measurement vector, and
   performing a sparse decomposition based on the measurement vector to estimate the composition of the food.

26. The system of claim 24, wherein estimating the composition of the identified food is further based on a second sensing matrix, the second sensing matrix comprising radar signatures of combinations of two or more types of foods.

27. A method for estimating a composition of food, the method comprising:
receiving radar data from an ADC of a millimeter-wave radar;
preprocessing the received radar data to generate a radar image;
generating a measurement vector based on the radar image; and
estimating a composition of the food based on the measurement vector and a predetermined first sensing matrix, the first sensing matrix comprising radar signatures of a plurality of types of food wherein each column of the first sensing matrix comprises a radar signature that corresponds to a particular type of food.

28. The method of claim 27, wherein the estimated composition of food comprises one or more types of food.

29. The method of claim 27, wherein estimating the composition of food is further based on a second sensing matrix, the second sensing matrix comprising radar signatures of combinations of two or more types of foods.

30. The method of claim 29, wherein the estimated composition of food comprises proportions of fats, proteins, and carbohydrates.

31. The method of claim 27, wherein estimating the composition of the food further comprises:
   performing a discrete cosine transform on the radar image to generate the measurement vector; and
   performing a sparse decomposition based on the measurement vector to estimate the composition of the food.

* * * * *